(12) United States Patent
Wolf et al.

(10) Patent No.: US 10,920,285 B2
(45) Date of Patent: Feb. 16, 2021

(54) **HIGHLY SPECIFIC AND SENSITIVE METHODS FOR DETECTING ENTEROHEMORRHAGIC *ESCHERICHIA COLI* SEROTYPES O157:H7 AND/OR O145:H28**

(71) Applicant: QIAGEN GMBH, Hilden (DE)

(72) Inventors: Kathrin Wolf, Hilden (DE); Sascha Strauss, Hilden (DE)

(73) Assignee: QIAGEN GMBH, Hilden (DE)

( * ) Notice: Subject to any disclaimer, the term of this patent is extended or adjusted under 35 U.S.C. 154(b) by 0 days.

(21) Appl. No.: 15/532,558

(22) PCT Filed: Dec. 3, 2015

(86) PCT No.: PCT/EP2015/078597
§ 371 (c)(1),
(2) Date: Jun. 2, 2017

(87) PCT Pub. No.: WO2016/087621
PCT Pub. Date: Jun. 9, 2016

(65) Prior Publication Data
US 2017/0362637 A1 Dec. 21, 2017

(30) Foreign Application Priority Data
Dec. 3, 2014 (EP) .................................. 14196070

(51) Int. Cl.
*C12Q 1/689* (2018.01)
*C12Q 1/6883* (2018.01)
(52) U.S. Cl.
CPC ........... *C12Q 1/689* (2013.01); *C12Q 1/6883* (2013.01)
(58) Field of Classification Search
None
See application file for complete search history.

(56) References Cited

U.S. PATENT DOCUMENTS

| 2006/0051769 A1 | 3/2006 | Barts |
| 2011/0020823 A1 | 1/2011 | Burns |

FOREIGN PATENT DOCUMENTS

| WO | WO-2010/132832 | 11/2010 |
| WO | WO-2013/186754 | 12/2013 |
| WO | PCT/EP2015/078597 | 12/2015 |
| WO | WO-2016/087621 | 6/2016 |

OTHER PUBLICATIONS

BLAST search of SEQ ID No. 10 nucleotides 380-400 preformed Feb. 17, 2020 on NCBI website (Year: 2020).*
Cooper et al., Comparative genomics of enterohemorrhagic *Escherichia coli* O145:H28 demonstrates a common evolutionary lineage with *Escherichia coli* O157:H7, BMC Genomics 15:17, (2014).
Beutin L. et al: "Evaluation of the 'GeneDisc' real-time PCR system for detection of enterohaemorrhagic *Escherichia coli* (EHEC) 026, 0103, 0111, 0145 and 0157 strains according to their virulence markers and their 0- and H-antigen-associated genes". Journal of Applied Microbiology, (2009) vol. 106. No. 4, pp. 1122-1132.
Bugarel, et al: "Virulence gene profiling of enterohemorrhagic (EHEC) and enteropathogenic (EPEC) *Escherichia coli* strains: a basis for molecular risk assessment of typical and atypical EPEC strains". BMC Microbiology. Biomed Central Ltd, (2011) vol. 11, No. 1, p. 142.
Madic, J., et al, "Simplex and Multiplex Real-Time PCR Assays for the Detection of Flagellar (H-antigen) Flic Alleles and Intimin (eae) Variants Associated with Enterohemorrhagic *Escherichia coli* (EHEC) Serotypes 026:h11, 0103:h2, 0111:h8, 0145:H28 and 0157:H7" Journal of Applied Microbiology, vol. 109, Jul. 1, 2010, pp. 1696-1705.
International Search Report and Written Opinion dated Feb. 29, 2016 by the International Searching Authority for International Application No. PCT/EP2015/078597, which was filed on Dec. 3, 2015 and published as WO 2016/087621 on Jun. 9, 2016 (Applicant—QIAGEN GMBH) (10 pages).
International Preliminary Report on Patentability dated Jun. 6, 2017 by the International Searching Authority for International Application No. PCT/EP2015/078597, which was filed on Dec. 3, 2015 and published as WO 2016/087621 on Jun. 9, 2016 (Applicant—QIAGEN GMBH) (6 pages).

* cited by examiner

*Primary Examiner* — Katherine D Salmon
(74) *Attorney, Agent, or Firm* — Ballard Spahr LLP

(57) ABSTRACT

The present invention relates to methods and kits for the specific detection of *Escherichia coli* (*E. coli*) serotypes O157:H7 and/or O145:H28. The methods and kits are based on the detection of newly identified sequence regions, which have a very high sequence identity between *E. coli* serotypes O157:H7 and O145:H28 and which are not present in any other known *E. coli* serotype or bacteria. This sequence region thus allows for selective detection of *E. coli* O157:1-17 and/or O145:H28 from other bacteria, especially other *E. coli* serotypes. Furthermore the present invention shows that a 3 bp InDel sequence in O157:H7 allows for distinguishing between O157:H7 and O145:H28, which allows for selective detection of O157:H7 over O145:H28 and vice versa. Furthermore, the invention provides oligonucleotides useful for said detection.

6 Claims, 4 Drawing Sheets

Specification includes a Sequence Listing.

HIGHLY SPECIFIC AND SENSITIVE METHODS FOR DETECTING ENTEROHEMORRHAGIC *ESCHERICHIA COLI* SEROTYPES O157:H7 AND/OR O145:H28

CROSS-REFERENCE TO RELATED PATENT APPLICATIONS

This application claims the benefit of priority under 35 U.S.C. § 371 of International Application No. PCT/EP2015/078597 filed on Dec. 3, 2015 which claims priority to European Application No. EP 14196070.8 filed on Dec. 3, 2014. The content of these earlier filed applications is hereby incorporated by reference in their entirety.

SEQUENCE LISTING

The present application contains a Sequence Listing that has been submitted in text format via EFS-Web, containing the file name 17104_0062U1_SL.txt which is 4,976 bytes in size, created on May 17, 2017, and is hereby incorporated by reference pursuant to 37 C.F.R. § 1.52(e)(5).

FIELD OF THE INVENTION

The present invention relates to methods and kits for the specific detection of *Escherichia coli* (*E. coli*) serotypes O157:H7 and/or O145:H28. The methods and kits are based on the detection of newly identified sequence regions, which have a very high sequence identity between *E. coli* serotypes O157:H7 and O145:H28 and which are not present in any other known *E. coli* serotype or bacteria. This sequence region thus allows for selective detection of *E. coli* O157:H7 and/or O145:H28 from other bacteria, especially other *E. coli* serotypes. Furthermore, the present invention shows that a 3 bp InDel sequence in O157:H7 allows for distinguishing between O157:H7 and O145:H28, which allows for selective detection of O157:H7 over O145:H28 and vice versa. Furthermore, the invention provides oligonucleotides useful for said detection.

BACKGROUND OF THE INVENTION

Detection of pathogenic *E. coli* as a food contaminant has become a major public health priority. In particular, the serotypes O157:H7 and O145:H28 belong to a group of *E. coli* strains, which are most frequently associated with human foodborne illness worldwide. *E. coli* serotype O157:H7 causes enterohemorrhagic colitis and possibly kidney failure. Only very recently, Cooper et al., *BMC Genomics* 15:17, 2014, identified the genome sequence of the *E. coli* strain O145:H28, which has been associated with foodborne enterohemorrhagic outbreaks in the USA (RM13514) and Belgium (RM13516). In addition, both O157:H7 and O145:H28 are subject to testing by the US Department of Agriculture (USDA) with a zero tolerance standard: In the US, regulations require meat processors to screen for the presence of O157:H7 and O145:H28 in their finished products. Consequently, a test for a rapid, specific and sensitive detection of these highly pathogenic O157:H7 and/or O145:H28 *E. coli* serotypes in a sample is extremely important for both public health and from an economic perspective. Genomic comparisons reveal that *E. coli* serotype O157:H7 has evolved stepwise from serotype O55:H7, which is associated with infantile diarrhea.

WO 2010/132832 A1 and US 2011/0020823 A1 describe the identification of *E. coli* serotype O157:H7, based on the detection of a combination of at least two O157:H7-specific sequences. Furthermore, the methods of both documents require samples enriched with *E. coli* serotype O157:H7 for detection.

Thus, there is a need in the art for simpler, more specific and more sensitive tools and methods for the detection of *E. coli* serotypes O157:H7 and/or O145:H28.

SUMMARY OF THE INVENTION

The present invention relates to methods and kits for the specific detection of *E. coli* serotype O157:H7 and/or O145:H28 over other *E. coli* serotypes, as well as other bacteria. Furthermore, it also allows for selective detection of O157:H28 serotype over *E. coli* serotype O145:H28. Similarly, it also allows for selective detection of O145:H28 serotype over *E. coli* O157:H7. In particular, the invention is based on the identification of a new polynucleotide sequence within the genome of *E. coli* serotypes O157:H7, i.e. SEQ ID NO:10 and of *E. coli* serotype O145:H28, i.e. SEQ ID NO: 11. The invention is furthermore based on the recognition that the detection of said sequences, or of specific parts of those sequences, in a sample, will provide for a simple, highly specific and sensitive test for the presence of *E. coli* serotypes O157:H7 and/or O145:H28, respectively, or for polynucleotides specific therefor, in that sample.

Thus, the present invention provides polynucleotides comprising or consisting of the nucleotide sequence depicted herein as SEQ ID NOs:10 or 11, or a nucleotide sequence that is the complement of SEQ ID NOs:10 or 11, respectively. For example, such polynucleotides are polynucleotides that do not represent the complete genomic DNA of *E. coli*, and in particular not the complete genomic DNA of enterohemorrhagic *E. coli* O157:H7 or *E. coli* O145:H28. Preferably, the polynucleotide of the invention is a plasmid or a cosmid. It can also be a vector, such as a viral vector or a phage vector. In a preferred embodiment, the polynucleotide of the invention has a maximum length of 50 kb. More preferred are lengths of 20 kb, 10 kb, 5 kb, 2 kb, and even more particularly 1 kb. Particularly preferred is a length of 0.8 kb, or a length that is identical, or almost identical (e.g., with a few additional nucleotides at the 3' and/or 5' end, e.g., 2 additional nucleotides, or 1 additional nucleotide) to SEQ ID NOs:10 or 11 or the nucleotide sequence that is the complement of SEQ ID NOs:10 or 11, or is a double-stranded nucleic acid formed by the nucleotide sequence of SEQ ID NOs:10 or 11 and its complement.

Further, the present invention provides oligonucleotides for specific detection of O157:H7 and/or O145:H28. These oligonucleotides are preferably suitable for detecting, e.g., in a sample, enterohemorrhagic *E. coli* O157:H7 and/or O145:H28, respectively.

In particular, some oligonucleotides distinguish *E. coli* O157:H7 and/or O145:H28, or nucleic acids specific therefor, over other *E. coli* serotypes. In preferred embodiments, the oligonucleotides are additionally capable of distinguishing *E. coli* O157:H7 over O145:H28 and *E. coli* O145:H28 over O157:H7, respectively.

For example, oligonucleotides of the invention will be capable of hybridizing under stringent conditions to a nucleotide sequence within SEQ ID NOs:10 or 11, or to a nucleotide sequence that is complementary thereto.

Alternatively, an oligonucleotide of the invention will have a nucleotide sequence that is at least 80%, preferably 90%, more preferably 95%, even more preferably 98%, and particularly preferably 99% identical to a nucleotide sequence of the same length within SEQ ID NO: 10 or within SEQ ID NO:11, or to the complement of said nucleotide sequences of the same length. Particularly preferred is an oligonucleotide that is identical to a nucleotide sequence of the same length within SEQ ID NO:10 or within SEQ ID NO: 11, respectively, or to the complement of said nucleotide sequences of the same length.

Preferred oligonucleotides of the invention can be used as a probe or as a primer to specifically detect, e.g., in a sample, *E. coli* serotype O157:H7 or nucleic acid specific therefor, such as *E. coli* serotype O157:H7 genomic DNA. In particularly preferred embodiments, the oligonucleotides are capable of distinguishing between *E. coli* serotype O157:H7 and non-O157:H7 *E. coli* serotypes, including *E. coli* serotype O145:H28.

In analogy to the above, other preferred oligonucleotides of the invention can be used as a probe or as a primer to specifically detect, e.g., in a sample, *E. coli* serotype O145:H28, or nucleic acid specific therefor, such as *E. coli* serotype O145:H28 genomic DNA. Accordingly, in another preferred embodiment, the oligonucleotide is capable of distinguishing between *E. coli* serotype O145:H28 and non-O145:H28 *E. coli* serotypes, including *E. coli* serotype O157:H7.

It will be appreciated that this suitability and/or capability is due to the fact that the oligonucleotide will specifically hybridize under stringent hybridization conditions to nucleotide sequences that are specific for *E. coli* serotypes O157:H7 and/or O145:H28 compared to said other *E. coli* serotypes, or the fact that the nucleotide sequence of the oligonucleotide comprises, or consists of, a corresponding *E. coli* serotype O157:H7 and/or O145:H28 specific nucleotide sequence, respectively.

Thus, for example, a preferred oligonucleotide of the invention will specifically hybridize under stringent conditions to the corresponding sequence within *E. coli* serotype O157:H7 or O145:H28 specific nucleic acids, but not to *E. coli* serotype O145:H28 or O157:H7 specific nucleic acid, respectively. In particular, preferred oligonucleotides of the invention will specifically hybridize under stringent conditions to the corresponding sequence within *E. coli* serotype O157:H7 or O145:H28 genomic DNA, but not to *E. coli* serotype O145:H28 or O157:H7 genomic DNA, respectively.

Particularly preferred for the specific detection of *E. coli* serotype O157:H7 is an oligonucleotide where said nucleotide sequence or said nucleotide sequence complementary thereto to which said oligonucleotide hybridizes, comprises nucleotides 382-385 of SEQ ID NO:10 or the complement of nucleotides 382-385 of SEQ ID NO:10, respectively. Likewise particularly preferred is thus an oligonucleotide where said sequence of the same length within SEQ ID NO:10 or its complement, to which the nucleotide sequence of the oligonucleotide is identical, or at least 80%, preferably 90%, more preferably 95%, even more preferably 98%, and particularly preferably 99% identical, comprises nucleotides 382-385 of SEQ ID NO:10 or the complement of nucleotides 382-385 of SEQ ID NO:10, respectively.

In particularly preferred embodiments, an isolated oligonucleotide suitable for detecting enterohemorrhagic *E. coli* O157:H7, or nucleic acid specific therefor
  (a) is capable of hybridizing under stringent conditions to a nucleotide sequence within SEQ ID NO:10, or to a nucleotide sequence that is complementary thereto;
  (b) has a nucleotide sequence that is at least 80% identical to a nucleotide sequence of the same length within SEQ ID NO:10, or to the complement of said nucleotide sequence of the same length;
  (c) has a nucleotide sequence that is at least 90% identical to a nucleotide sequence of the same length within SEQ ID NO:10, or to the complement of said nucleotide sequence of the same length;
  (d) has a nucleotide sequence that is at least 95% identical to a nucleotide sequence of the same length within SEQ ID NO:10, or to the complement of said nucleotide sequence of the same length;
  (e) has a nucleotide sequence that is at least 98% identical to a nucleotide sequence of the same length within SEQ ID NO:10, or to the complement of said nucleotide sequence of the same length;
  (f) has a nucleotide sequence that is at least 99% identical to a nucleotide sequence of the same length within SEQ ID NO:10, or to the complement of said nucleotide sequence of the same length; or
  (g) has a nucleotide sequence that is identical to a nucleotide sequence of the same length within SEQ ID NO:10, or to the complement of said nucleotide sequence of the same length,
wherein said nucleotide sequence or said nucleotide sequence complementary thereto to which said oligonucleotide hybridizes, or wherein the sequence of the same length or its complement, comprise nucleotides 382-385 of the nucleotide sequence of SEQ ID NO:10 or the complement of nucleotides 382-385, respectively.

In other particularly preferred embodiments, an isolated oligonucleotide suitable for detecting enterohemorrhagic *E. coli* O157:H7, or nucleic acid specific therefor
  (a) is capable of hybridizing under stringent conditions to a nucleotide sequence within SEQ ID NO:10, or to a nucleotide sequence that is complementary thereto;
  (b) has a nucleotide sequence that is at least 80% identical to a nucleotide sequence of the same length within SEQ ID NO:10, or to the complement of said nucleotide sequence of the same length;
  (c) has a nucleotide sequence that is at least 90% identical to a nucleotide sequence of the same length within SEQ ID NO:10, or to the complement of said nucleotide sequence of the same length;
  (d) has a nucleotide sequence that is at least 95% identical to a nucleotide sequence of the same length within SEQ ID NO:10, or to the complement of said nucleotide sequence of the same length;
  (e) has a nucleotide sequence that is at least 98% identical to a nucleotide sequence of the same length within SEQ ID NO:10, or to the complement of said nucleotide sequence of the same length;
  (f) has a nucleotide sequence that is at least 99% identical to a nucleotide sequence of the same length within SEQ ID NO:10, or to the complement of said nucleotide sequence of the same length; or
  (g) has a nucleotide sequence that is identical to a nucleotide sequence of the same length within SEQ ID NO:10, or to the complement of said nucleotide sequence of the same length,
wherein said nucleotide sequence or said nucleotide sequence complementary thereto to which said oligonucleotide hybridizes, or wherein the sequence of the same length or its complement, comprise nucleotides 382-385 of the nucleotide sequence of SEQ ID NO:10 or the complement of nucleotides 382-385, respectively, with the proviso that said oligonucleotide does not have the sequence of SEQ ID NO:14.

Particularly preferred for the specific detection of *E. coli* serotype O145:H28 is an oligonucleotide, where said nucleotide sequence or said nucleotide sequence complementary thereto, to which said oligonucleotide hybridizes, comprises nucleotides 384-388 of SEQ ID NO:11 or the complement of nucleotides 384-388 of SEQ ID NO:11, respectively. Accordingly, likewise particularly preferred is also an oligonucleotide where said sequence of the same length within SEQ ID NO:11 or its complement, to which the nucleotide sequence of the oligonucleotide is identical, or at least 80%, preferably 90%, more preferably 95%, even more preferably 98%, and particularly preferably 99% identical, comprises nucleotides 384-388 of SEQ ID NO:11 or the complement of nucleotides 384-388 of SEQ ID NO:11, respectively.

In particularly preferred embodiments, an isolated oligonucleotide suitable for detecting enterohemorrhagic *E. coli* O145:H28, or nucleic acid specific therefor (a) is capable of hybridizing under stringent conditions to a nucleotide sequence within SEQ ID NO:11, or to a nucleotide sequence that is complementary thereto;

(b) has a nucleotide sequence that is at least 80% identical to a nucleotide sequence of the same length within SEQ ID NO:11, or to the complement of said nucleotide sequence of the same length;

(c) has a nucleotide sequence that is at least 90% identical to a nucleotide sequence of the same length within SEQ ID NO:11, or to the complement of said nucleotide sequence of the same length;

(d) has a nucleotide sequence that is at least 95% identical to a nucleotide sequence of the same length within SEQ ID NO:11, or to the complement of said nucleotide sequence of the same length;

(e) has a nucleotide sequence that is at least 98% identical to a nucleotide sequence of the same length within SEQ ID NO:11, or to the complement of said nucleotide sequence of the same length;

(f) has a nucleotide sequence that is at least 99% identical to a nucleotide sequence of the same length within SEQ ID NO:11, or to the complement of said nucleotide sequence of the same length; or (g) has a nucleotide sequence that is identical to a nucleotide sequence of the same length within SEQ ID NO:11, or to the complement of said nucleotide sequence of the same length, wherein said nucleotide sequence or said nucleotide sequence complementary thereto, to which said oligonucleotide hybridizes, or wherein the sequence of the same length or its complement, comprise nucleotides 384-388 of the nucleotide sequence of SEQ ID NO:11 or the complement of nucleotides 384-388, respectively.

Also, a single primer or probe oligonucleotide for the simultaneous detection of O157:H7 and O145:H28 serotypes over other *E. coli* serotypes and other bacteria may comprise any sequence which is identical between SEQ ID NO:10 and SEQ ID NO:11, their complement, a fragment thereof, or any sequence having at least 80%, preferably 90%, more preferably 95%, even more preferably 98%, and particularly preferably 99% identity with these.

In highly preferred embodiments for selective O157:H7 detection, the oligonucleotide of the invention has a nucleotide sequence selected from the nucleotide sequences of SEQ ID NOs:1, 2, and 6. In highly preferred embodiments for selective O145:H28 detection, the oligonucleotide of the invention has a nucleotide sequence selected from the nucleotide sequences of SEQ ID NOs:12 and 13.

The invention further provides methods for detection of enterohemorrhagic *E. coli* O157:H7, or nucleic acids specific therefor, in a sample, wherein the methods comprise:

(i) performing an amplification reaction using at least one oligonucleotide suitable for detecting enterohemorrhagic *E. coli* O157:H7, or nucleic acid specific therefor, wherein said oligonucleotide (a) is capable of hybridizing under stringent conditions to a nucleotide sequence within SEQ ID NO:10, or to a nucleotide sequence that is complementary thereto;

(b) has a nucleotide sequence that is at least 80% identical to a nucleotide sequence of the same length within SEQ ID NO:10, or to the complement of said nucleotide sequence of the same length;

(c) has a nucleotide sequence that is at least 90% identical to a nucleotide sequence of the same length within SEQ ID NO:10, or to the complement of said nucleotide sequence of the same length;

(d) has a nucleotide sequence that is at least 95% identical to a nucleotide sequence of the same length within SEQ ID NO:10, or to the complement of said nucleotide sequence of the same length;

(e) has a nucleotide sequence that is at least 98% identical to a nucleotide sequence of the same length within SEQ ID NO:10, or to the complement of said nucleotide sequence of the same length;

(f) has a nucleotide sequence that is at least 99% identical to a nucleotide sequence of the same length within SEQ ID NO:10, or to the complement of said nucleotide sequence of the same length; or (g) has a nucleotide sequence that is identical to a nucleotide sequence of the same length within SEQ ID NO:10, or to the complement of said nucleotide sequence of the same length, wherein said nucleotide sequence or said nucleotide sequence complementary thereto to which said oligonucleotide hybridizes, or wherein the sequence of the same length or its complement, comprise nucleotides 382-385 of the nucleotide sequence of SEQ ID NO:10 or the complement of nucleotides 382-385, respectively; and optionally (ii) determining the presence of an amplification product.

The invention further provides methods for detection of enterohemorrhagic O145:H28, or nucleic acids specific therefor, in a sample, wherein the methods comprise:

(i) performing an amplification reaction using at least one oligonucleotide suitable for detecting enterohemorrhagic *E. coli* O145:H28, or nucleic acid specific therefor, wherein said oligonucleotide (a) is capable of hybridizing under stringent conditions to a nucleotide sequence within SEQ ID NO:11, or to a nucleotide sequence that is complementary thereto;

(b) has a nucleotide sequence that is at least 80% identical to a nucleotide sequence of the same length within SEQ ID NO:11, or to the complement of said nucleotide sequence of the same length;

(c) has a nucleotide sequence that is at least 90% identical to a nucleotide sequence of the same length within SEQ ID NO:11, or to the complement of said nucleotide sequence of the same length;

(d) has a nucleotide sequence that is at least 95% identical to a nucleotide sequence of the same length within SEQ ID NO:11, or to the complement of said nucleotide sequence of the same length;

(e) has a nucleotide sequence that is at least 98% identical to a nucleotide sequence of the same length within SEQ ID NO:11, or to the complement of said nucleotide sequence of the same length;

(f) has a nucleotide sequence that is at least 99% identical to a nucleotide sequence of the same length within SEQ ID NO:11, or to the complement of said nucleotide sequence of the same length; or (g) has a nucleotide sequence that is identical to a nucleotide sequence of the same length within SEQ ID NO:11, or to the complement of said nucleotide sequence of the same length, wherein said nucleotide sequence or said nucleotide sequence complementary thereto, to which said oligonucleotide hybridizes, or wherein the sequence of the same length or its complement, comprise nucleotides 384-388 of the nucleotide sequence of SEQ ID NO:11 or the complement of nucleotides 384-388, respectively; and optionally (ii) determining the presence of an amplification product.

The invention also provides methods for detection of enterohemorrhagic O145:H28 and O157:H7, or nucleic acids specific therefor, in a sample, wherein the methods comprise:

(i) performing an amplification reaction using at least one oligonucleotide suitable for detecting enterohemorrhagic *E. coli* O157:H7 and O145:H28, or nucleic acid specific therefor, wherein said oligonucleotide (a) is capable of hybridizing under stringent conditions to a nucleotide sequence within SEQ ID NO:10 and SEQ ID NO:11, or to a nucleotide sequence that is complementary thereto;

(b) has a nucleotide sequence that is at least 80% identical to a nucleotide sequence of the same length within SEQ ID NO:10 and SEQ ID NO:11, or to the complement of said nucleotide sequence of the same length;

(c) has a nucleotide sequence that is at least 90% identical to a nucleotide sequence of the same length within SEQ ID NO:10 and SEQ ID NO:11, or to the complement of said nucleotide sequence of the same length;

(d) has a nucleotide sequence that is at least 95% identical to a nucleotide sequence of the same length within SEQ ID NO:10 and SEQ ID NO:11, or to the complement of said nucleotide sequence of the same length;

(e) has a nucleotide sequence that is at least 98% identical to a nucleotide sequence of the same length within SEQ ID NO:10 and SEQ ID NO:11, or to the complement of said nucleotide sequence of the same length; or (f) has a nucleotide sequence that is at least 99% identical to a nucleotide sequence of the same length within SEQ ID NO:10 and SEQ ID NO:11, or to the complement of said nucleotide sequence of the same length; and optionally (ii) determining the presence of an amplification product.

In preferred embodiments, a pair of oligonucleotides in accordance with the invention is used as amplification primers for performing the amplification reaction. Further, it will be appreciated that also two or even more pairs of oligonucleotides of the invention may be used as primers in this regard.

It will furthermore be appreciated that detection of an amplification product in the course of the method of the invention will be indicative of the presence of *E. coli* O157:H7 and/or O145:H28, or of nucleic acids specific therefor, in the sample.

The methods for the detection of enterohemorrhagic O157:H7 and/or O145:H28 may further optionally comprise a probe, wherein said probe (hybridization probe) hybridizes with a fragment of the target sequence, such as SEQ ID NO:10 and/or SEQ ID NO:11, or complements thereof, respectively. Preferably, the probe hybridizes with a fragment of SEQ ID NO: 10 and/or SEQ ID NO: 11, located between the hybridization sites of the forward and the reverse primers, or complements thereof. In highly preferred embodiments the nucleotide sequence of said probe does not overlap with the nucleotide sequence of said primers.

In preferred embodiments, the probe hybridizes with a nucleotide fragment within the nucleotides 264-485 of SEQ ID NO: 10 and/or within the nucleotides 264-488 of SEQ ID NO:11, or complements thereof, respectively. In even more preferred embodiments the oligonucleotide sequence of the probe is selected from, but not restricted to SEQ ID NOs: 7-9.

In highly preferred embodiments, the probe is used in methods having primer oligonucleotides as amplification primers for the detection of O157:H7, wherein at least one primer oligonucleotide or oligonucleotide sequence complementary thereto, to which said primer oligonucleotide hybridizes, comprises nucleotides 382-385 of the nucleotide sequence of SEQ ID NO:10 or the complement of nucleotides 382-385, respectively.

In other highly preferred embodiments, the probe is used in methods having primer oligonucleotides as amplification primers for the detection of O145:H28, wherein at least one primer oligonucleotide or oligonucleotide sequence complementary thereto, to which said primer oligonucleotide hybridizes, comprises nucleotides 384-388 of the nucleotide sequence of SEQ ID NO:11 or the complement of nucleotides 384-388, respectively.

In yet other highly preferred embodiments, the probe is used in methods having primer oligonucleotides as amplification primers for the detection of O157:H7 and O145:H28, wherein at least one primer oligonucleotide or oligonucleotide sequence complementary thereto, to which said primer oligonucleotide hybridizes, comprises a sequence, which is identical between SEQ ID NO:10 and SEQ ID NO:11, their complement, a fragment thereof, or any sequence having at least 80%, preferably 90%, more preferably 95%, even more preferably 98%, and particularly preferably 99% identity with these.

The amplification method used in accordance with the invention may be a polymerase chain reaction (PCR) or any other amplification method, such as a ligase chain reaction, a ligase detection reaction, SDA, 3SR, NASBA, TMA, and the like. Preferably, the amplification method is PCR. In more preferred embodiments, the PCR is real-time PCR.

The invention also provides a kit for the detection of *E. coli* O157:H7, or nucleic acid specific therefor, in a sample, wherein the kit comprises:

(i) one or more oligonucleotides as amplification primers, wherein said one or more oligonucleotide(s)

(a) is/are capable of hybridizing under stringent conditions to a nucleotide sequence within SEQ ID NO:10, or to a nucleotide sequence that is complementary thereto;

(b) has/have a nucleotide sequence that is at least 80% identical to a nucleotide sequence of the same length within SEQ ID NO:10, or to the complement of said nucleotide sequence of the same length;

(c) has/have a nucleotide sequence that is at least 90% identical to a nucleotide sequence of the same length within SEQ ID NO:10, or to the complement of said nucleotide sequence of the same length;

(d) has/have a nucleotide sequence that is at least 95% identical to a nucleotide sequence of the same length within SEQ ID NO:10, or to the complement of said nucleotide sequence of the same length;

(e) has/have a nucleotide sequence that is at least 98% identical to a nucleotide sequence of the same length within SEQ ID NO:10, or to the complement of said nucleotide sequence of the same length;
(f) has/have a nucleotide sequence that is at least 99% identical to a nucleotide sequence of the same length within SEQ ID NO:10, or to the complement of said nucleotide sequence of the same length; or
(g) has/have a nucleotide sequence that is identical to a nucleotide sequence of the same length within SEQ ID NO:10, or to the complement of said nucleotide sequence of the same length, wherein said nucleotide sequence or said nucleotide sequence complementary thereto to which said oligonucleotide hybridizes, or wherein the sequence of the same length or its complement, comprise nucleotides 382-385 of the nucleotide sequence of SEQ ID NO:10 or the complement of nucleotides 382-385, respectively; and optionally
(ii) a polymerase, preferably a DNA polymerase.

Similarly, the invention also provides a kit for the detection of E. coli O145:H28, or nucleic acid specific therefor, in a sample, wherein the kit comprises:
(i) one or more oligonucleotides as amplification primers; wherein said one or more oligonucleotide(s)
(a) is/are capable of hybridizing under stringent conditions to a nucleotide sequence within SEQ ID NO:11, or to a nucleotide sequence that is complementary thereto;
(b) has/have a nucleotide sequence that is at least 80% identical to a nucleotide sequence of the same length within SEQ ID NO:11, or to the complement of said nucleotide sequence of the same length;
(c) has/have a nucleotide sequence that is at least 90% identical to a nucleotide sequence of the same length within SEQ ID NO:11, or to the complement of said nucleotide sequence of the same length;
(d) has/have a nucleotide sequence that is at least 95% identical to a nucleotide sequence of the same length within SEQ ID NO:11, or to the complement of said nucleotide sequence of the same length;
(e) has/have a nucleotide sequence that is at least 98% identical to a nucleotide sequence of the same length within SEQ ID NO:11, or to the complement of said nucleotide sequence of the same length;
(f) has/have a nucleotide sequence that is at least 99% identical to a nucleotide sequence of the same length within SEQ ID NO:11, or to the complement of said nucleotide sequence of the same length; or
(g) has/have a nucleotide sequence that is identical to a nucleotide sequence of the same length within SEQ ID NO:11, or to the complement of said nucleotide sequence of the same length, wherein said nucleotide sequence or said nucleotide sequence complementary thereto, to which said oligonucleotide hybridizes, or wherein the sequence of the same length or its complement, comprise nucleotides 384-388 of the nucleotide sequence of SEQ ID NO:11 or the complement of nucleotides 384-388, respectively; and optionally
(ii) a polymerase, preferably a DNA polymerase.

Additionally, the invention also provides a kit for the detection of E. coli O157:H7 and O145:H28, or nucleic acid specific therefor, in a sample, wherein the kit comprises: (i) one or more oligonucleotides as amplification primers, wherein said one or more oligonucleotide(s)
(a) is/are capable of hybridizing under stringent conditions to a nucleotide sequence within SEQ ID NO:10 and SEQ ID NO:11, or to a nucleotide sequence that is complementary thereto;
(b) has/have a nucleotide sequence that is at least 80% identical to a nucleotide sequence of the same length within SEQ ID NO:10 and SEQ ID NO:11, or to the complement of said nucleotide sequence of the same length;
(c) has/have a nucleotide sequence that is at least 90% identical to a nucleotide sequence of the same length within SEQ ID NO:10 and SEQ ID NO:11, or to the complement of said nucleotide sequence of the same length;
(d) has/have a nucleotide sequence that is at least 95% identical to a nucleotide sequence of the same length within SEQ ID NO:10 and SEQ ID NO:11, or to the complement of said nucleotide sequence of the same length;
(e) has/have a nucleotide sequence that is at least 98% identical to a nucleotide sequence of the same length within SEQ ID NO:10 and SEQ ID NO:11, or to the complement of said nucleotide sequence of the same length; or
(f) has/have a nucleotide sequence that is at least 99% identical to a nucleotide sequence of the same length within SEQ ID NO:10 and SEQ ID NO:11, or to the complement of said nucleotide sequence of the same length; and optionally
(ii) a polymerase, preferably a DNA polymerase.

Additionally, or alternatively to the polymerase, the kit may comprise a negative control sample, e.g. a sample lacking any E. coli O157:H7 and/or O145:H28, or any nucleic acid specific therefor.

Again additionally, or alternatively to the polymerase and/or the negative control sample, the kit may comprise a positive control sample, e.g. a sample containing E. coli O157:H7 and/or O145:H28, or nucleic acid specific therefor.

The kits for the detection of enterohemorrhagic O157:H7 and/or O145:H28 may further optionally comprise a probe, wherein said probe (hybridization probe) hybridizes with a fragment within the target sequence, such as SEQ ID NO:10 and/or SEQ ID NO:11, or complements thereof, respectively. Preferably, the probe hybridizes with a fragment within SEQ ID NO: 10 and/or SEQ ID NO: 11, located between the hybridization sites of the forward and the reverse primers, or complements thereof. In highly preferred embodiments the nucleotide sequence of said probe does not overlap with the nucleotide sequence of said primers.

In preferred embodiments, the probe hybridizes with a nucleotide fragment within the nucleotides 264-485 of SEQ ID NO: 10 and/or within the nucleotides 264-488 of SEQ ID NO:11, or complements thereof, respectively. In even more preferred embodiments the oligonucleotide sequence of the probe is selected from, but not restricted to SEQ ID NOs: 7-9.

In highly preferred embodiments, the probe is used in kits having primer oligonucleotides as amplification primers for the detection of O157:H7, wherein at least one primer oligonucleotide or oligonucleotide sequence complementary thereto, to which said primer oligonucleotide hybridizes, comprises nucleotides 382-385 of SEQ ID NO:10 or the complement of nucleotides 382-385, respectively.

In other highly preferred embodiments, the probe is used in kits having primer oligonucleotides as amplification primers for the detection of O145:H28, wherein at least one primer oligonucleotide or oligonucleotide sequence complementary thereto, to which said primer oligonucleotide hybridizes, comprises nucleotides 384-388 of SEQ ID NO:11 or the complement of nucleotides 384-388, respectively.

The methods of this invention are highly sensitive and thus the methods and the kits of this invention may also be conducted without enrichment of E. coli O157:H7 and/or O145:H28, or nucleic acid specific therefor, in the samples to be analyzed. The methods and kits described herein can detect E. coli O157:H7 and/or O145:H28, or nucleic acids specific therefor, in samples that contain as few as about 10 copies of the genomic DNA of the organism to be analyzed.

The oligonucleotides of the invention may have a length of about 10-100 nucleotides (in particular 10-24 and 26-100 nucleotides). Preferred is an oligonucleotide of 10-50 nucleotides (in particular 10-24 and 26-50 nucleotides). More preferred is an oligonucleotide that has a length of about 10-30 nucleotides (in particular 10-24 and 26-30 nucleotides), more preferably of 18-27 nucleotides. In even more preferred embodiments, the oligonucleotide length is selected from, but not restricted to 18-24 nucleotides and 26-27 nucleotides.

In most preferred embodiments, a primer oligonucleotide has a length of 20 nucleotides. Likewise most preferred is a length of 27 nucleotides. Further likewise most preferred primer oligonucleotides have a length of 18 or 24 nucleotides.

In preferred embodiments, a probe oligonucleotide has a length of 18-27 nucleotides. In even more preferred embodiments, a probe oligonucleotide has a length of 25 nucleotides. Likewise preferred is an oligonucleotide that has a length of 23 nucleotides.

The oligonucleotides of the invention may optionally comprise a label such as a fluorescent dye, particularly if used as probes or primers, e.g., primers in amplification reactions. TaqMan probes modified with fluorescent dyes such as 6-FAM, MAX, HEX, ROX, Texas Red or Cy5.5 or any other fluorescent dye at the 5'-end in combination with a quencher moiety at the 3'-end such as IBFQ, BHQ-1, BHQ-2, or any other suited quenchers could be used.

Sources of the samples analyzed using the methods and kits of the invention may be water, food, feces, or any other sample potentially comprising E. coli O157:H7 and/or O145:H28. The sample may or may not be enriched with bacterial cells, or bacterial nucleic acid. The bacteria to be analyzed using the methods and kits of the invention may be isolated from the sample, the bacteria may be lysed, and/or the DNA may be extracted.

Finally, it will be appreciated that the present invention also encompasses the use of the oligonucleotides and kits described and/or claimed herein for the detection of enterohemorrhagic E. coli O157:H7 and/or O145:H28, or nucleic acids specific therefor. This includes, of course, the use of the oligonucleotides and kits described and/or claimed herein in the methods described and/or claimed herein.

BRIEF DESCRIPTION OF THE DRAWINGS

FIG. 1A shows amplification curves of E. coli O157:H7 DNA by real-time PCR assay runs with template DNA originating from E. coli O157:H7 strain (DSM_13526), wherein at least one primer is selected from oligonucleotide of SEQ ID NOs:1.
FIG. 1B shows amplification curves of an internal amplification control, which comprises an artificial plasmid, corresponding primers, and a probe, which are added to the reaction mix, whereby said internal control demonstrates that the PCR works correctly when positive results are achieved for the E. coli inclusivity test and when negative results are achieved for the E. coli exclusivity test.

FIG. 2A illustrates real-time PCR curves with DNA templates originating from non-E. coli O157:H7 strains wherein at least one primer is selected from oligonucleotides of SEQ ID NOs:1, 2 and 6.
FIG. 2B shows amplification curves of an added internal amplification control, which comprises an artificial plasmid, corresponding primers, and a probe, which are added to the reaction mix, whereby said internal control demonstrates that the PCR works correctly when positive results are achieved for the E. coli exclusivity test.

FIG. 3 shows Ct (cycle threshold) values for real-time PCR assay for E. coli O157:H7 DNA amplification, wherein the cycle threshold defines the number of cycles required for the fluorescence signal to cross the threshold or the background level. O157:H7-DNA-dilutions of 10, 100, 1.000, or 10.000 copies of O157:H7-DNA were used per reaction in order to determine the respective Ct values.

FIG. 4 illustrates amplification curves for E. coli O157:H7 real-time PCR assay runs with DNA dilutions originating from E. coli O157:H7 strain (DSM 13526) by using O157:H7-DNA solutions comprising 10, 100, 1,000, or 10,000 copies of O157:H7-DNA per reaction.

DETAILED DESCRIPTION OF THE INVENTION

Definitions

Figure 1:
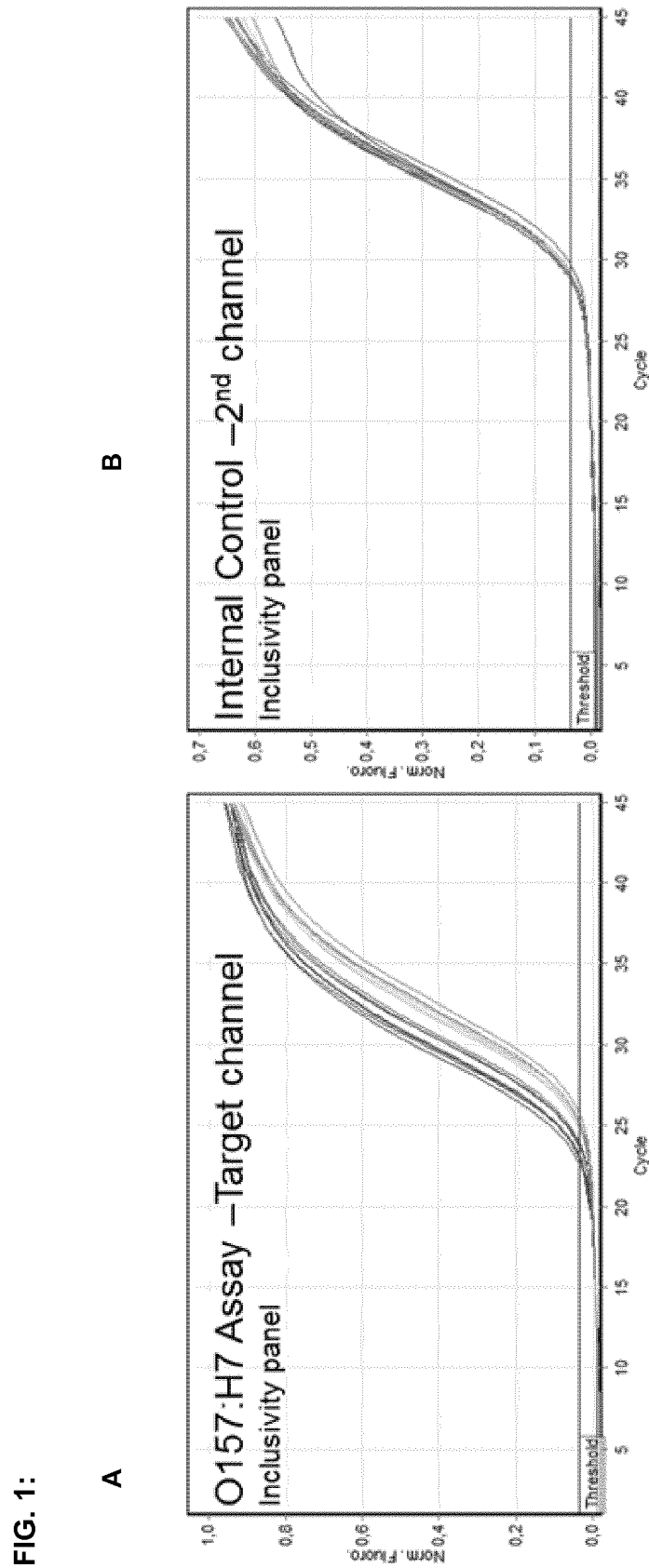
FIG. 1.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry).

In practicing the present invention, many conventional techniques in molecular biology, microbiology, and recombinant DNA may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods In Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

The term "other E. coli serotypes" includes all currently known E. coli serotypes in the art, except for O157:H7, O145:H28, or both.

In preferred embodiments "other E. coli serotypes than O157:H7" include, but are not restricted to any one of the following: O1:H7, O1:K1:H7, O19:H7, O26:H-, O26:H7, O45:H-SSI 81886, O55:H7 E. coli ref. Center 10.0728, O55:H7 E. coli ref. Center 9.0106, O55:H7 ECRC EQ5624-50 6/96, O7:K1:H7, O103:H-, O111:H-, O121:H7 from human, O121:H7 from beef, O121 NC09121, O145 SSI 82280, O153:H7 from rabbit, O157:H16, O157:H38 HEALTH CANADA 03/14/00, O157:H38 WILD 03/09/00, O157:H45, O157:H19 CDC 1924-82 03/09/00, O157:NM, O18ac:K1:H7, *Escherichia coli* VTEC T3 (stx1), and *Escherichia coli* VTEC T6 (stx2).

In preferred embodiments "other *E. coli* serotypes than O145:H28" include, but are not restricted to any one of the following: O1:H7, O1:K1:H7, O19:H7, O26:H-, O26:H7, O45 SSI 81886, O55:H7 *E. coli* ref. Center 10.0728, O55:H7 *E. coli* ref. Center 9.0106, O55:H7 ECRC EQ5624-50 6/96, O7:K1:H7, O103:H-, O111:H-, O121:H7 from human, O121:H7 from beef, O121 NC09121, O153:H7 from rabbit, O157:H16, O157:H19, O157:H38 HEALTH CANADA 03/14/00, O157:H38 WILD 03/09/00, O157:H45, O157:H19 CDC 1924-82 03/09/00, O157:NM, O18ac:K1:H7, *Escherichia coli* VTEC T3 (stx1), *Escherichia coli* VTEC T6 (stx2), O157 NM *E. coli* ref. Center 0.0373, O157 NM *E. coli* ref. Center 88.1041, O157:H7 DSM_8579, O157:H7 DSM_13526, O157:H7 DSM_17076, and O157:H7 DSM 19206.

In preferred embodiments "other *E. coli* serotypes than O157:H7 and O145:H28" include, but are not restricted to any one of the following: O1:H7, O1:K1:H7, O19:H7, O26:H-, O26:H7, O45:H-SSI 81886, O55:H7 *E. coli* ref. Center 10.0728, O55:H7 *E. coli* ref. Center 9.0106, O55:H7 ECRC EQ5624-50 6/96, O7:K1:H7, O103:H-, O111:H-, O121:H7 from human, O121:H7 from beef, O121 NC09121, O153:H7 from rabbit, O157:H16, O157:H19, O157:H38 HEALTH CANADA 03/14/00, O157:H38 WILD 03/09/00, O157:H45, O157:H19 CDC 1924-82 03/09/00, O157:NM, 018ac:K1:H7, *Escherichia coli* VTEC T3 (stx1), and *Escherichia coli* VTEC T6 (stx2).

As used herein, the term "about" when used together with a numerical value (e.g., a pH value or a percentage value) is intended to encompass a deviation of 20%, preferably 10%, more preferably 5%, even more preferably of 2%, and most preferably of 1% from that value. When used together with a numerical value it is at the same time to be understood as individually disclosing that exact numerical value as a preferred embodiment in accordance with the present invention.

As used herein, the term "comprising" is to be construed as encompassing both "including" and "consisting of", both meanings being specifically intended, and hence individually disclosed, embodiments in accordance with the present invention.

"nt" is an abbreviation of "nucleotides".

"PCR" is an abbreviation of polymerase chain reaction.

The term "primer" refers to an oligonucleotide (synthetic or occurring naturally) that is capable of acting as a point of initiation of nucleic acid synthesis or replication along a complementary strand when placed under conditions in which synthesis of a complementary strand is catalyzed by a polymerase.

The term "hybridization" refers to a process of establishing a non-covalent, sequence-specific interaction between two or more complementary strands of nucleic acids into a single complex, which in the case of two strands is referred to as a double-stranded DNA or duplex.

The phrase "stringent hybridization conditions" refers to hybridization conditions which can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. By varying the conditions (especially salt concentration and temperature) a given primer or probe sequence may be allowed to hybridize only with its exact complement or with any somewhat related sequences. Increasing the temperature and/or decreasing the salt concentration will tend to increase the selectivity of a hybridization reaction, and thus will raise the stringency. Under conditions of "high stringency" (for example: high temperature and/or low salt concentration), only exact matches of bases will anneal and stay together. To achieve high stringency in the amplification techniques described herein, e.g. PCR, the annealing temperature of the primers/probes is usually about 5° C. less than the melting temperature, ensuring that only the desired target is amplified.

"Label" refers to a molecule attached to an oligonucleotide (covalently or non-covalently) and capable of providing information about the oligonucleotide it is attached to, including, but not limited to, radioactive isotopes, fluorophores, chemiluminescent reagents, dyes, enzymes, enzyme substrates, or semiconductor nanocrystals, such as quantum dots. Labels can provide a detectable (and optionally quantifiable) signal.

"Locus" is a specific DNA sequence on the bacterial chromosome.

The term "hybridization probe" refers to a DNA fragments that are synthesized to hybridize to a specific locus present in a target amplified region of the DNA to span a site containing a mutation or polymorphism. In some preferred embodiments, the hybridization probes are labeled with one or more fluorescent labels. In other preferred embodiments the hybridization probes are labeled with a fluorescence label and a fluorescence quencher. In preferred embodiments the probe hybridizes with a fragment of SEQ ID NO:10 and/or SEQ ID NO:11. In even more preferred embodiments, the probe hybridizes with a fragment within SEQ ID NO:10 and/or SEQ ID NO:11, located between the hybridization sites of the forward and the reverse primers, or complements thereof. In highly preferred embodiments, the nucleotide sequence of said probe does not overlap with the nucleotide sequence of said primers.

In even more preferred embodiments, the probe hybridizes with a nucleotide fragment within the nucleotides 264-485 of SEQ ID NO:10 and/or within the nucleotides 264-488 of SEQ ID NO:11, or complements thereof, respectively.

In some embodiments, one hybridization probe is used. In some embodiments, two or more hybridization probes are used. Said hybridization probes are described in more detail elsewhere in the description.

A "quencher" is a molecule, which absorbs the energy transferred from a fluorescent label (also called a reporter), and thus quenches the emitted light by the reporter. Said energy transfer generates the excited state of the quencher. Subsequently, the excited state of the quencher decays radiatively at another, higher wavelength. Alternatively, the quencher decays non-radiatively (dark quencher).

The term "fragment" refers to any sequence within SEQ ID NO: 10 having 10-699 nt (nucleotides) in length or to any sequence within SEQ ID NO: 11 having 10-702 nt in length. The length of a fragment for the detection of O157:H7 and/or O145:H28 serotypes is characterized by the amplification product by using forward and reverse primers of this invention for detecting *E. coli* serotypes O157:H7 and/or O145:H28.

In preferred embodiments, the fragment for the detection of O157:H7 serotype in a sample has a length of about 30-699, 50-600, 70-500, 100-400, or 120-300 nt within SEQ ID NO: 10. In more preferred embodiments, the fragment has a length of about 125-275 nt within SEQ ID NO:10. In highly preferred embodiments the fragment length has a length of about 129-271 nt within SEQ ID NO:10. Most preferably, said fragment comprises the nucleotides 382-385 of SEQ ID NO:10.

In preferred embodiments, the fragment for the detection of O145:H28 serotype in a sample has a length of about 30-702, 50-600, 70-500, 100-400, or 120-300 nt within SEQ ID NO: 11. In more preferred embodiments, the fragment has a length of about 125-275 nt within SEQ ID NO:11. In highly preferred embodiments the fragment has a length of about 129-274 nt within SEQ ID NO:11. Most preferably, said fragment comprises the nucleotides 384-388 of SEQ ID NO:11.

"InDel" describes a mutation resulting in both an insertion of nucleotides and a deletion of nucleotides, which results in a net change in the total number of nucleotides, where both changes are nearby on the DNA.

"Target sequence or target DNA" refers to a nucleic acid of interest. The target sequence can be a polynucleotide sequence that is subject to hybridization with a complementary nucleotide, such as a primer oligonucleotide or a polynucleotide. The target sequence may be SEQ ID NO:10, a complement or a fragment thereof when selectively detecting the presence of the E. coli serotype O157:H7 by using oligonucleotides, which hybridize with SEQ ID NO:10, as well as methods and kits referred to herein, which are specific for E. coli serotype O157:H7 detection. In particular, hybridization with 382-385 of SEQ ID NO:10 is indicative of the presence of E. coli O157:H7.

The "target sequence" may also be SEQ ID NO:11, a complement, or a fragment thereof when selectively detecting the presence of the E. coli serotype O145:H28 by using oligonucleotides, which hybridize with SEQ ID NO:11, as well as methods and kits referred to herein, which are specific for E. coli serotype O145:H28 detection. In particular, hybridization with 384-388 of SEQ ID NO:11 is indicative of the presence of E. coli O145:H28.

Accordingly, the term "target E. coli strain" refers to E. coli serotype O157:H7 and/or to E. coli serotype O145:H28.

"Nucleic acid specific for enterohemorrhagic E. coli strain O157:H7" or "O157:H7 specific" refers to a nucleic acid or a complement thereof that comprises nucleotide sequences which are found only in genomic DNA of enterohemorrhagic E. coli strain O157:H7. Nucleic acid specific for enterohemorrhagic E. coli strain O157:H7 as referred to herein is thus nucleic acid that distinguishes those strains containing it as, or as part of, their genomic DNA from the majority of other E. coli strains. Preferably, the nucleic acid specific for enterohemorrhagic E. coli strain O157:H7 according to the invention is nucleic acid that contains, or consists of, nucleotide sequences which are found only in genomic DNA of enterohemorrhagic E. coli strain O157:H7, but not in any non-O157:H7 E. coli serotype.

Similarly, "the nucleic acid specific for enterohemorrhagic E. coli strain O145:H28" or "O145:H28 specific" refers to a nucleic acid or a complement thereof that contains, or consists of, nucleotide sequences which are found only in genomic DNA of enterohemorrhagic E. coli strain O145:H28 and E. coli serotype O145:H28. In an even more preferred embodiment, the nucleic acid specific for enterohemorrhagic E. coli strain O145:H28 according to the invention is nucleic acid that contains, or consists of, nucleotide sequences which are found only in genomic DNA of enterohemorrhagic E. coli strain O145:H28, but not in any non-O145:H28 E. coli serotype.

The term "oligonucleotides specific for enterohemorrhagic E. coli strain O157:H7" includes, but is not restricted to oligonucleotides that hybridize with 382-385 of SEQ ID NO:10 or a complement thereof, such as SEQ ID NOs:1, 2, and 6.

The term "oligonucleotides specific for enterohemorrhagic E. coli strain O145:H28 includes, but is not restricted to oligonucleotides that hybridize with 384-388 of SEQ ID NO:11 or a complement thereof, such as SEQ ID NOs:12 and 13.

The term "oligonucleotide specific for O157:H7 and O145:H28" refers to any of the following sequences: SEQ ID NOs:10, 11, and any oligonucleotide within SEQ ID NOs:10 and 11 and complements thereof, except for sequences, which comprise any of nucleotides 382-385 of SEQ ID NO:10 and nucleotides 384-388 of SEQ ID NO:11, respectively. Such nucleotides include, but are not restricted to SEQ ID NO: 3.

The term "melting temperature" of an oligonucleotide is the temperature, at which 50% of the oligonucleotide and its perfect complement are double-stranded.

"Annealing" refers to pairing of complementary sequences of single-stranded DNA or RNA by hydrogen bonds to form a double-stranded polynucleotide. The term is often used to describe the binding of a DNA probe or the binding of a primer oligonucleotide to a DNA strand during a polymerase chain reaction.

"Quenching" refers to any process which decreases the fluorescence intensity of a florescent reagent caused by a second moiety (quencher).

"Molecular beacons" refer to sequence-specific oligonucleotides of about 25-40 nucleotides that form a hairpin structure with a stem and a loop, wherein a fluorescent molecule is attached to the 5' or 3' end and a quencher is attached to the 3' or 5' end, respectively. Formation of the hairpin brings the fluorescent molecule and quencher together, so that no fluorescence is emitted. The loop of the hairpin is designed to hybridize to 15-30 nucleotides of the target sequence. During the annealing step of the amplification reaction by using two PCR primers, the loop of the molecular beacon hybridizes to the target sequence. As a consequence, the fluorescent molecule and the quencher are separated, and the fluorescence is detectable.

"Dual hybridization probes" comprise two sequence-specific oligonucleotide probes in addition to two sequence-specific PCR primers. The two probes are designed to hybridize to adjacent sequences of the target DNA. The probes are labeled with a pair of dyes that allow for fluorescence resonance energy transfer (FRET). The donor dye is e.g. attached to the 3' end of the first probe, while the acceptor dye is attached to the 5' end of the second probe.

The term "FRET" refers to a phenomenon that is generally known as the fluorescence resonance energy transfer, where energy is transferred between two light-sensitive molecules, which are in close proximity.

"Eclipse probe" refers to a sequence-specific oligonucleotide that is labeled with a fluorescent molecule at the 3' or 5' end combined with a quencher and a minor groove binder at the 5' or 3' end, respectively. Its sequence is complementary to the target sequence. Corresponding assays comprise said eclipse probe and two PCR primers. During the annealing phase of a PCR, the probe hybridizes to the target with the help of the minor-groove binder. The probe becomes linearized, and the reporter and the quencher become separated. The resulting fluorescence signal is proportional to the amount of amplified product in the sample.

"Scorpions Primers®" are applied in PCR assays for improved detection of amplified DNA in a PCR reaction. Said assays comprise an unlabeled PCR primer and a primer comprising a stem-loop structure with a fluorescent molecule at the 5' end and a quencher at the 3' end ("Scorpions primer"®). The loop includes a sequence that is complementary to a part of the target sequence. During the first amplification cycle, the Scorpions PCR primer is extended. During subsequent amplification cycles the loop of the Scorpions probe hybridizes to the internal target sequence, whereby the fluorescent molecule is separated from the quencher. The resulting fluorescence signal is proportional to the amount of amplified product.

"LUX™ primers" are used together with a second PCR primer for an improved detection of DNA amplification. The LUX™ primer has a hairpin-shaped secondary structure with a fluorescent molecule attached near the 3' end. The hairpin-structure acts as a fluorescence quencher. During amplification, the LUX™ PCR primer is anneals to single-stranded DNA, so that fluorescence is emitted.

The term "hydrolysis format" refers to a fluorescence detection method for real-time PCR, wherein an oligonucleotide labeled with a fluorophore at its 5'-end and a fluorescence quencher labeled at its 3' end, are separated by hydrolysis by the 5'→3' exonuclease activity of a Taq polymerase. As a result, fluorescence is emitted.

The term "inclusivity" is defined as the correct positive signal of target DNA samples, which allows for detecting the target pathogen, here O157:H7 and/or O145:H28.

The term "exclusivity" is defined as the correct lack of signal of non-target DNA samples and correct positive signal of an internal amplification control.

"Cycle threshold" defines the number of cycles required for the fluorescence signal to cross the threshold or the background level.

The term "threshold" refers to a value above the background and significantly below the plateau of an amplification plot. It must be placed within the linear region of the amplification curve, which represents the detectable log-linear range of the PCR. The threshold value should be set within the logarithmic amplification plot view to enable easy identification of the log-linear phase of the PCR. If several targets are used in the real-time experiment, the threshold must be set for each target.

Oligo- and Polynucleotides

The present invention provides an assay for a rapid and highly specific detection method of *E. coli* serotypes O157:H7 and/or O145:H28, wherein preferably only one oligonucleotide/primer or oligonucleotide/primer pair is sufficient for unambiguous detection of O157:H7 and/or O145:H28, respectively. The molecular detection assay of the invention targets a single, so far unidentified, sequence region of 700 nucleotides that is unique to O157:H7 among *E. coli*, in particular, as well as among bacteria in, and which allows for discrimination of O157:H7 serotype over other *E. coli* serotypes, such as O55:H7 or O145:H28, as well as other bacteria. The molecular detection assay of the invention targets a single, so far unidentified, sequence region of 700 nucleotides, in particular the region of 382-385 of SEQ ID NO:10.

*E. coli* serotype O145:H28 comprises a highly identical 703 nucleotide sequence region to *E. coli* serotype O157:H7 with a distinguishing feature, which allows for discrimination of O145:H28 over O157:H7 as well as other *E. coli* serotypes and bacteria. Said feature comprises a contiguous 3 nucleotide-insertion, TAA, which is located between nucleotides 383 and 384 of SEQ ID NO:10, corresponding to the nucleotides 384-386 of SEQ ID NO:11, followed by an identical nucleotide at position 387 (G) of SEQ ID NO:11 (SEQ ID NO:10 position 384), and a T to C replacement at O145:H28 position 388, when compared to SEQ ID NO:10 (position 385). Accordingly, the molecular detection assay of the invention targets a single, so far unidentified, sequence region of 703 nucleotides, in particular the region of 384-388 of SEQ ID NO:11.

Oligonucleotide primers or probes that target the sequence portion, which is identical between SEQ ID NOs: 10 and 11, may be used for kits and methods for the detection of *E. coli* serotypes O157:H7 and O145:H28 over all other *E. coli* serotypes and other bacteria.

Moreover, this assay is highly sensitive and may also be conducted without enrichment of *E. coli* O157:H7 and/or O145:H28, or nucleic acid specific therefor, in the samples to be analyzed. The method and kits described herein can detect *E. coli* O157:H7 and/or O145:H28, or nucleic acids specific therefor, in samples that contain as few as about 10 copies of the genomic DNA of the target organism.

Identification of the newly identified sequence regions was achieved by a thorough comparison of publicly available genome sequences from different *E. coli* strains. The genomic DNA sequences of *E. coli* O157:H7 or O145:H28 were split into overlapping subsequences of 200 nt length. Each subsequence was used as a query for a BLAST (Altshul et al. Nucleic Acids Res. 1; 25(17), 1997) search against the genomic DNA sequences of non-O157:H7 serotypes. These analyses revealed a locus (a specific DNA sequence on the bacterial chromosome) that contains a 3 nt-Insertion/Deletion specific for *E. coli* O157:H7. O145:H28 has a highly identical sequence to O157:H7, except for a contiguous 5 nucleotide sequence, TAAGC, positioned at nucleotides 384-388 of SEQ ID NO:11. The corresponding region within SEQ ID NO:10 is the 3 nt Insertion/Deletion specific for *E. coli* O157:H7, which is located between the nucleotides 383 and 384 of SEQ ID NO:10.

Multiple oligonucleotides were designed to target these loci. The oligonucleotides target the newly identified sequence region to achieve discrimination of O157:H7 over non-O157:H7 serotypes as well as to achieve discrimination of O145:H28 over non-O145:H28 serotypes. Sensitivity and specificity of candidate designs were tested bioinformatically by performing in silico PCRs using all sequences contained in the public nucleotide sequence database provided by the Nation Center for Biotechnology Information (NCBI) as target and confirmed with wet lab experiments.

For specific O157:H7 detection, the oligonucleotides of the invention specifically hybridize to the nucleotide sequence of SEQ ID NO:10 or its complement. In preferred embodiments, the sequence to which the primers or oligonucleotides of the invention hybridize comprises nucleotides 382-385 of SEQ ID NO:10 or the complement thereof. Accordingly, for specific O145:H28 detection, the oligonucleotides of the invention specifically hybridize to the nucleotide sequence of SEQ ID NO:11 or its complement. In preferred embodiments, the sequence to which the primers or oligonucleotides of the invention hybridize comprises nucleotides 384-388 of SEQ ID NO:11 or the complement thereof.

In some embodiments, the primer or the probe oligonucleotide has a length of 10-100 nucleotides (in particular 10-24 and 26-100 nucleotides). In preferred embodiments, the primer or the probe oligonucleotide has a length of 10-50 nucleotides (in particular 10-24 and 26-50 nucleotides), more preferred 10-30 nucleotides (in particular 10-24 and 26-30 nucleotides). In even more preferred embodiments, the oligonucleotide has a length of 18-27 nucleotides. In even more preferred embodiments, the oligonucleotide length is selected from, but not restricted to about 18-24 nucleotides and 26-27 nucleotides.

In most preferred embodiments, a primer oligonucleotide has a length of 20 nucleotides. Likewise even more preferred is a length of 27 nucleotides. Further likewise most preferred primer oligonucleotides have a length of 18 or 24 nucleotides.

In preferred embodiments, a probe oligonucleotide has a length of 18-27 nucleotides. In even more preferred embodiments, a probe oligonucleotide has a length of 25 nucleotides. Likewise preferred is an oligonucleotide that has a length of 23 nucleotides.

In further preferred embodiments, the oligonucleotides of the invention hybridize to their target sequence under high stringency conditions.

In some embodiments for O157:H7 detection, the primer or the oligonucleotide is selected from the oligonucleotide sequences of SEQ ID NOs:1, 2, and 6. In preferred embodiments, the forward primer is selected from the oligonucleotide sequences of SEQ ID NOs:1 and 2 and the reverse primer is selected from the oligonucleotide sequences of SEQ ID NOs:4 and 5. In further preferred embodiments, the forward primer is the oligonucleotide sequence of SEQ ID NO:3 and the reverse primer is the oligonucleotide sequence of SEQ ID NO:6.

In other embodiments for O145:H28 detection, the primer or oligonucleotide is selected from the oligonucleotide sequences of SEQ ID NOs:12 and 13. In preferred embodiments, the forward primer is the oligonucleotide sequence of SEQ ID NO:12 and the reverse primer is selected from the oligonucleotide sequences of SEQ ID NOs:4 and 5. In further preferred embodiments, the forward primer is the oligonucleotide sequence of SEQ ID NO:3 and the reverse primer is the oligonucleotide sequence of SEQ ID NO:13.

In some embodiments for O157:H7 and O145:H28 detection, the forward primer is selected from the oligonucleotide sequences of SEQ ID NO:3 and the reverse primer is selected from the oligonucleotide sequences of SEQ ID NOs: 4 and 5.

In some embodiments for O157:H7 and/or O145:H28 detection, an oligonucleotide hybridization probe is selected from within the sequence to be amplified by using the above primers selective for O157:H7 and/or O145:H28 detection. In preferred embodiments the probe is selected from SEQ ID NOs:7-9.

Methods

The invention also provides methods for detection of enterohemorrhagic *E. coli* O157:H7 and/or O145:H28, or nucleic acids specific therefor. Such methods may be based on the detection of hybridization of one of the oligonucleotides of the invention to a target sequence within SEQ ID NO:10 and/or SEQ ID NO:11 or the complement thereof, that may be found in genomic DNA of enterohemorrhagic *E. coli* strain O157:H7 and/or O145:H28, respectively. The method may also be based on the detection of an amplification product resulting from an amplification reaction performed using a primer oligonucleotide, or pair of primer oligonucleotides, of the invention.

In preferred embodiments, the method for detection of enterohemorrhagic *E. coli* O157:H7 comprises:

(i) performing an amplification reaction using at least one oligonucleotide suitable for detecting enterohemorrhagic *E. coli* O157:H7, or nucleic acid specific therefor, wherein said oligonucleotide
  (a) is capable of hybridizing under stringent conditions to a nucleotide sequence within SEQ ID NO:10, or to a nucleotide sequence that is complementary thereto;
  (b) has a nucleotide sequence that is at least 80% identical to a nucleotide sequence of the same length within SEQ ID NO:10, or to the complement of said nucleotide sequence of the same length;
  (c) has a nucleotide sequence that is at least 90% identical to a nucleotide sequence of the same length within SEQ ID NO:10, or to the complement of said nucleotide sequence of the same length;
  (d) has a nucleotide sequence that is at least 95% identical to a nucleotide sequence of the same length within SEQ ID NO:10, or to the complement of said nucleotide sequence of the same length;
  (e) has a nucleotide sequence that is at least 98% identical to a nucleotide sequence of the same length within SEQ ID NO:10, or to the complement of said nucleotide sequence of the same length;
  (f) has a nucleotide sequence that is at least 99% identical to a nucleotide sequence of the same length within SEQ ID NO:10, or to the complement of said nucleotide sequence of the same length; or
  (g) has a nucleotide sequence that is identical to a nucleotide sequence of the same length within SEQ ID NO:10, or to the complement of said nucleotide sequence of the same length,
wherein said nucleotide sequence or said nucleotide sequence complementary thereto to which said oligonucleotide hybridizes, or wherein the sequence of the same length or its complement, comprise nucleotides 382-385 of the nucleotide sequence of SEQ ID NO:10 or the complement of nucleotides 382-385, respectively; and optionally
(ii) determining the presence of an amplification product.

In preferred embodiments, the method for specific detection of enterohemorrhagic *E. coli* O145:H28 comprises:

(i) performing an amplification reaction using at least one oligonucleotide suitable for detecting enterohemorrhagic *E. coli* O145:H28, or nucleic acid specific therefor, wherein said oligonucleotide
  (a) is capable of hybridizing under stringent conditions to a nucleotide sequence within SEQ ID NO:11, or to a nucleotide sequence that is complementary thereto;
  (b) has a nucleotide sequence that is at least 80% identical to a nucleotide sequence of the same length within SEQ ID NO:11, or to the complement of said nucleotide sequence of the same length;
  (c) has a nucleotide sequence that is at least 90% identical to a nucleotide sequence of the same length within SEQ ID NO:11, or to the complement of said nucleotide sequence of the same length;
  (d) has a nucleotide sequence that is at least 95% identical to a nucleotide sequence of the same length within SEQ ID NO:11, or to the complement of said nucleotide sequence of the same length;
  (e) has a nucleotide sequence that is at least 98% identical to a nucleotide sequence of the same length within SEQ ID NO:11, or to the complement of said nucleotide sequence of the same length;
  (f) has a nucleotide sequence that is at least 99% identical to a nucleotide sequence of the same length within SEQ ID NO:11, or to the complement of said nucleotide sequence of the same length; or (g) has a nucleotide sequence that is identical to a nucleotide sequence of the same length within SEQ ID NO:11, or to the complement of said nucleotide sequence of the same length, wherein said nucleotide sequence or said nucleotide sequence complementary thereto, to which said oligonucleotide hybridizes, or wherein the sequence of the same length or its complement, comprise nucleotides 384-388 of the nucleotide sequence of SEQ ID NO:11 or the complement of nucleotides 384-388, respectively; and optionally (ii) determining the presence of an amplification product.

In some embodiments, the above methods for the detection of enterohemorrhagic O157:H7 or enterohemorrhagic O145:H28 may be carried out simultaneously for the detection of O157:H7 and O145:H28, preferably in a single vessel.

The invention also provides methods for detection of enterohemorrhagic O145:H28 and O157:H7, or nucleic acids specific therefor, in a sample, wherein the methods comprise:

(i) performing an amplification reaction using at least one oligonucleotide suitable for detecting enterohemorrhagic *E. coli* O157:H7 and O145:H28, or nucleic acid specific therefor, wherein said oligonucleotide
  (a) is capable of hybridizing under stringent conditions to a nucleotide sequence within SEQ ID NO:10 and SEQ ID NO:11, or to a nucleotide sequence that is complementary thereto;
  (b) has a nucleotide sequence that is at least 80% identical to a nucleotide sequence of the same length within SEQ ID NO:10 and SEQ ID NO:11, or to the complement of said nucleotide sequence of the same length;
  (c) has a nucleotide sequence that is at least 90% identical to a nucleotide sequence of the same length within SEQ ID NO:10 and SEQ ID NO:11, or to the complement of said nucleotide sequence of the same length;
  (d) has a nucleotide sequence that is at least 95% identical to a nucleotide sequence of the same length within SEQ ID NO:10 and SEQ ID NO:11, or to the complement of said nucleotide sequence of the same length;
  (e) has a nucleotide sequence that is at least 98% identical to a nucleotide sequence of the same length within SEQ ID NO:10 and SEQ ID NO:11, or to the complement of said nucleotide sequence of the same length; or
  (f) has a nucleotide sequence that is at least 99% identical to a nucleotide sequence of the same length within SEQ ID NO:10 and SEQ ID NO:11, or to the complement of said nucleotide sequence of the same length; and optionally (ii) determining the presence of an amplification product.

Amplification of the target polynucleotide is indicative of the presence of target *E. coli* serotype O157:H7 and/or O145:H28, respectively.

Most notably, it has been found for detection methods referred to in this invention that only one primer, or primer pair is sufficient for specific detection of the presence of *E. coli* O157:H7, O145:H28, or both. Therefore, in preferred embodiments, only one pair of primers is used in the detection methods of the invention.

In some embodiments, two or more primer pairs are selected for amplifying and detecting two distinct target sequences for the detection of O157:H7, O145:H28, or both.

In some embodiments for O157:H7-detection, at least two primer pairs are selected for amplifying and detecting two distinct target sequences within SEQ ID NO:10, whereby at least one of the two primers is selected from an oligonucleotide sequence of SEQ ID NOs:1, 2, or 6.

In some embodiments for O145:H28-detection, at least two primer pairs are selected for amplifying and detecting two distinct target sequences within SEQ ID NO:11, whereby at least one of the two primers is selected from an oligonucleotide sequence of SEQ ID NOs:12 or 13.

Hybridization of said first pair and second pair of oligonucleotide primers may occur in a single vessel or in two separate vessels.

In some embodiments, the methods for O157:H7- and/or O145:H28-detection may further comprise an oligonucleotide hybridization probe, which is selected from within the amplified sequence by using the above primers. In preferred embodiments the oligonucleotide sequence of the probe is selected from, but not restricted to SEQ ID NOs:7-9.

The amplification reaction may be a ligase chain reaction, a ligase detection reaction, or a polymerase chain reaction (PCR). In preferred embodiments, the polymerase chain reaction is a PCR, even more preferably a real-time PCR. In addition to PCR, the methods of the invention may be easily adapted to other primer extension amplification methods (e.g., SDA, 3SR, NASBA, TMA, etc.).

A typical PCR amplification cycle involves a denaturing phase where the target dsDNA melts, a primer annealing phase where the temperature is optimal for the primers to bind to the now-single-stranded target, and a chain elongation phase where the temperature is optimal for DNA polymerase to function. The denaturing phase is typically carried out at 94-98° C., preferably about 94-96° C., or even more preferably at about 95° C., The optimal primer hybridization or annealing temperature is dependent on the base composition (i.e., the proportion of A, T, G, and C nucleotides), primer concentration, the temperature for optimal polymerase activity, and ionic reaction environment. It is about 5° C. below the melting temperature of a calculated melting temperature of an oligonucleotide, which can be calculated by the person skilled in the art by applying the teachings by e.g. Santa Lucia, *Proc. Natl. Acad. Sci. Vol.* 95, p. 1460-1465, 1998. Said temperature for PCR oligonucleotides is typically between about 50-68° C., preferably about 52-65° C., more preferably about 55-62° C., even more preferably about 58-61° C., or it is most preferably about 60° C.

The chain elongation phase is preferably carried out at about 68-72° C. under consideration of the typical extension rate of a polymerase at 1 min/kb. Each cycle and thus multiple cycles of a PCR reaction may be carried out by using an automated thermal cycler.

The number of PCR cycle reactions depends e.g. on the amount of the copies of template nucleic acid in a real-time PCR reaction. The number of cycles for analyzing the samples described herein is at least 40-50 cycles, more preferably at least 45 cycles.

The primer oligonucleotide concentration in the methods or kits of this invention is typically 0.1-1.0 µM for each primer oligonucleotide, wherein in preferred embodiments the concentration is 0.1-0.8 µM, 0.1-0.7 µM, 0.15-0.4 µM, or 0.2 µM.

The amplification reaction may be carried out in solution or on a solid support, such as nitrocellulose, or a microarray. In preferred embodiments, the sample to be analyzed may be immobilized on a solid support, such as a silicon chip or a microarray.

Detection of an amplified target sequence may be conducted by any standard method known to the skilled person. Detection may be carried out inter alia after multiple amplification cycles have been run (end-point-PCR) or during each amplification cycle (real-time PCR). DNA analysis methods include, but are not restricted to, fluorescence detection, capillary electrophoresis and gel electrophoresis, southern blotting, and sequencing of amplified DNA.

Real-time PCR is routinely carried out by using labels, such as fluorophores, to facilitate the signal detection and quantification of amplified nucleic acid. One or more fluorescent molecules may be applied that either bind to the amplified product or that are attached to primer oligonucleotides or hybridization probes of a PCR reaction.

Any oligonucleotide or primer of this invention may comprise one or more labels, which are selected from a dye, a radioactive isotope, and a chemiluminescent label, wherein preferably the label is a fluorescent dye, which is optionally linked to a quencher, as described elsewhere in this invention.

The fluorescent dye may be selected from a cyanine, rhodamine, fluorescein, acriflavin, acridine orange, fluorescent coumarine-derivatives, and any fluorescent derivatives thereof. In preferred embodiments the fluorescent dye is a cyanine or a derivative thereof. In even more preferred embodiments the fluorescent dye is Cy5.5. Suitable examples for fluorescent dyes binding double-stranded DNA are selected from, but not restricted to: SYBR® Green I, SYBR® Green II, SYBR® Gold, SYBR® Safe, Oxazole Yellow, Thiazole Orange, and PicoGreen.

Suitable examples for fluorescent dyes that can be coupled to oligonucleotides comprise a suitable coupling agent including, but not limited to, N-hydroxysuccinimidyl (NHS)-ester group. Any sequence-specific oligonucleotides of this invention may be labeled with a single fluorescent dye, with two fluorescent dyes, or a fluorescent dye and a fluorescence quencher. Examples for fluorescence quenchers are selected from, but not restricted to TAMRA™ and Black Hole Quenchers®, such as BHQ-0, BHQ-1, BHQ-2, and BHQ-3, preferably BHQ-2. In some embodiments said oligonucleotides may be used as primer oligonucleotides for PCR and/or the primers may be used as hybridization probes, which anneal to a single-stranded DNA-template during the PCR. Examples for such hybridization probes include, but are not restricted to hydrolysis (TaqMan) probes, molecular beacons, dual hybridization probes, eclipse probes, scorpions Primers®, and LUX™ primers.

Accordingly, by using said fluorescent dyes and said labeling methods, real-time PCR can be carried out in several assays known to the person skilled in the art, which are e.g. dyes binding to amplified double-stranded DNA, hydrolysis assays, such as Taq Man®, and hybridization assays, such as FRET hybridization and usage of single labeled probes. When carrying out multiple PCR reactions in one reaction vessel, dyes with the widest channel separation possible are used to avoid any potential signal crosstalk.

Kits

The invention also provides kits for detection of *E. coli* O157:H7, or nucleic acid specific therefor, in a sample, wherein the kits comprise:
 (i) one or more oligonucleotides as amplification primers, wherein said one or more oligonucleotide(s)
  (a) is/are capable of hybridizing under stringent conditions to a nucleotide sequence within SEQ ID NO:10, or to a nucleotide sequence that is complementary thereto;
  (b) has/have a nucleotide sequence that is at least 80% identical to a nucleotide sequence of the same length within SEQ ID NO:10, or to the complement of said nucleotide sequence of the same length;
  (c) has/have a nucleotide sequence that is at least 90% identical to a nucleotide sequence of the same length within SEQ ID NO:10, or to the complement of said nucleotide sequence of the same length;
  (d) has/have a nucleotide sequence that is at least 95% identical to a nucleotide sequence of the same length within SEQ ID NO:10, or to the complement of said nucleotide sequence of the same length;
  (e) has/have a nucleotide sequence that is at least 98% identical to a nucleotide sequence of the same length within SEQ ID NO:10, or to the complement of said nucleotide sequence of the same length;
  (f) has/have a nucleotide sequence that is at least 99% identical to a nucleotide sequence of the same length within SEQ ID NO:10, or to the complement of said nucleotide sequence of the same length; or
  (g) has/have a nucleotide sequence that is identical to a nucleotide sequence of the same length within SEQ ID NO:10, or to the complement of said nucleotide sequence of the same length,
wherein said nucleotide sequence or said nucleotide sequence complementary thereto to which said oligonucleotide hybridizes, or wherein the sequence of the same length or its complement, comprise nucleotides 382-385 of the nucleotide sequence of SEQ ID NO:10 or the complement of nucleotides 382-385, respectively; and optionally
 (ii) a polymerase, preferably a DNA polymerase.

Similarly, the invention also provides kits for detection of *E. coli* O145:H28, or nucleic acid specific therefor, in a sample, wherein the kit comprises:
 (i) one or more oligonucleotides as amplification primers; wherein said one or more oligonucleotide(s)
  (a) is/are capable of hybridizing under stringent conditions to a nucleotide sequence within SEQ ID NO:11, or to a nucleotide sequence that is complementary thereto;
  (b) has/have a nucleotide sequence that is at least 80% identical to a nucleotide sequence of the same length within SEQ ID NO:11, or to the complement of said nucleotide sequence of the same length;
  (c) has/have a nucleotide sequence that is at least 90% identical to a nucleotide sequence of the same length within SEQ ID NO:11, or to the complement of said nucleotide sequence of the same length;
  (d) has/have a nucleotide sequence that is at least 95% identical to a nucleotide sequence of the same length within SEQ ID NO:11, or to the complement of said nucleotide sequence of the same length;
  (e) has/have a nucleotide sequence that is at least 98% identical to a nucleotide sequence of the same length within SEQ ID NO:11, or to the complement of said nucleotide sequence of the same length;
  (f) has/have a nucleotide sequence that is at least 99% identical to a nucleotide sequence of the same length within SEQ ID NO:11, or to the complement of said nucleotide sequence of the same length; or
  (g) has/have a nucleotide sequence that is identical to a nucleotide sequence of the same length within SEQ ID NO:11, or to the complement of said nucleotide sequence of the same length,
wherein said nucleotide sequence or said nucleotide sequence complementary thereto, to which said oligonucleotide hybridizes, or wherein the sequence of the same length or its complement, comprise nucleotides 384-388 of the nucleotide sequence of SEQ ID NO:11 or the complement of nucleotides 384-388, respectively; and optionally
 (ii) a polymerase, preferably a DNA polymerase.

Additionally, the invention also provides a kit for the detection of *E. coli* O157:H7 and O145:H28, or nucleic acid specific therefor, in a sample, wherein the kit comprises:

(i) one or more oligonucleotides as amplification primers; wherein said one or more oligonucleotide(s)

(a) is/are capable of hybridizing under stringent conditions to a nucleotide sequence within SEQ ID NO:10 and SEQ ID NO:11, or to a nucleotide sequence that is complementary thereto;

(b) has/have a nucleotide sequence that is at least 80% identical to a nucleotide sequence of the same length within SEQ ID NO:10 and SEQ ID NO:11, or to the complement of said nucleotide sequence of the same length;

(c) has/have a nucleotide sequence that is at least 90% identical to a nucleotide sequence of the same length within SEQ ID NO:10 and SEQ ID NO:11, or to the complement of said nucleotide sequence of the same length;

(d) has/have a nucleotide sequence that is at least 95% identical to a nucleotide sequence of the same length within SEQ ID NO:10 and SEQ ID NO:11, or to the complement of said nucleotide sequence of the same length;

(e) has/have a nucleotide sequence that is at least 98% identical to a nucleotide sequence of the same length within SEQ ID NO:10 and SEQ ID NO:11, or to the complement of said nucleotide sequence of the same length; or (f) has/have a nucleotide sequence that is at least 99% identical to a nucleotide sequence of the same length within SEQ ID NO:10 and SEQ ID NO:11, or to the complement of said nucleotide sequence of the same length; and optionally (ii) a polymerase, preferably a DNA polymerase.

The kits for the detection of *E. coli* O157:H7 and/or O145:H28 may further comprise a probe, wherein said probe hybridizes within the target sequence, which is amplified by the above amplification primers selective for *E. coli* O157:H7 and/or O145:H28 detection. In preferred embodiments the oligonucleotide sequence of the probe is selected from, but not restricted to SEQ ID NOs:7-9.

As noted above, the kits may alternatively, or in addition to the polymerase comprise a negative control sample and/or a positive control sample.

The *E. coli* O157:H7 negative control sample can be a nucleic acid that does not comprise SEQ ID NO:10 or its complement, or any fragment thereof. In preferred embodiments, the negative control sample does not comprise nucleotides 382-385 of SEQ ID NO:10 or the complement thereof. The positive control sample can be a nucleic acid comprising SEQ ID NO:10 or its complement, or any fragment thereof. In preferred embodiments, the positive control sample comprises nucleotides 382-385 of SEQ ID NO:10 or the complement thereof.

Accordingly, the *E. coli* O145:H28 negative control sample can be a nucleic acid that does not comprise SEQ ID NO:11 or its complement, or any fragment thereof. In preferred embodiments, the negative control sample does not comprise nucleotides 384-388 of SEQ ID NO:11 or the complement thereof. The positive control sample can be a nucleic acid comprising SEQ ID NO:11 or its complement, or any fragment thereof. In preferred embodiments, the positive control sample comprises nucleotides 384-388 of SEQ ID NO:11 or the complement thereof.

In a preferred embodiment, the kits referred to in this invention contain only one primer/oligonucleotide or only one pair of primers/oligonucleotides in accordance with the invention. However, the kits of the invention may also further comprise one or more additional pairs of primers in accordance with the invention.

The samples that can be analyzed by the methods or kits of the invention comprise water, food, or any other sample, such as an environmental sample from soil, dirt, garbage, sewage, air, food processing and manufacturing surfaces, or a biological sample, referring to a sample obtained from a prokaryotic or an eukaryotic source, such as feces, urine or blood, which samples may comprise *E. coli* O157:H7 and/or O145:H28.

Said samples may be enriched for *E. coli* O157:H7 and/or O145:H28 bacteria, or nucleic acid specific therefor, such as *E. coli* strain O157:H7 and/or O145:H28 genomic DNA. However, the methods of the invention are so sensitive that enrichment is not necessary. In preferred embodiments, the sample is therefore not enriched with *E. coli* O157:H7 and/or O145:H28 bacteria or nucleic acid, whereby only 10 copies of the target DNA are sufficient to selectively detect the target DNA.

The bacteria, i.e. O157:H7, O145:H28, as well as other *E. coli* and non-*E. coli* bacteria referred to herein, and exemplified in the examples section, may be isolated from a sample to be analyzed. The bacteria may be lysed, and/or the DNA may be extracted by any method known to the person skilled in the art prior to being analyzed by the method or kits of this invention. The isolation may be carried out, e.g., by isolating DNA from stool by using QIAamp® DNA Stool Mini Kit, isolation DNA from blood, cultures, and body fluids by using QIAamp® UCP Pathogen Mini kit, or isolating bacterial DNA from food or from pharmaceutical products for contamination analysis by using Mericon™ DNA Bacteria Kit.

All cited literature is fully incorporated herein by reference. Data shown in the methods and kits of this invention originates from one of the oligonucleotide/sample combinations, respectively, but is representative for all combinations. The examples below are thus intended to illustrate the invention, but not to limit its scope.

EXAMPLES

The following examples represent procedures that can be employed for the detection of *E. coli*.

Reactions for the inclusivity and exclusivity testing of O157:H7 were set up according to the following scheme:

10 µl 2× reconstituted PCR-Assay containing specific Primers/Probe, dNTPs,

HotStarTaq Plus DNA Polymerase and dedicated multiplex Realtime-PCR buffer+10 µl sample DNA (or positive, or negative control)

Cycling profile:

5 min 95° C. Initial PCR activation step followed by 3-step cycling (40-45 cycles)

15 s 95° C. Denaturation 15 s 60° C. Annealing 10 s 72° C. Extension

Inclusivity tests are carried out in Example 1 and illustrated in FIG. 1. In this context, inclusivity is defined as the correct positive signal of target DNA samples, which allows for detecting the target pathogen, here O157:H7.

The strains used in the inclusivity tests are shown in Table 1.

TABLE 1

| Organism | O group | H group | source (if known) comments | test result |
|---|---|---|---|---|
| *Escherichia coli* | O157 | NM/H7 | *E. coli* ref. Center 0.0373 | positive |
| *Escherichia coli* | O157 | NM/H7 | *E. coli* ref. Center 88.1041 | positive |
| *Escherichia coli* | O157 | H7 | DSM_8579 | positive |
| *Escherichia coli* | O157 | H7 | DSM_13526 | positive |
| *Escherichia coli* | O157 | H7 | DSM_17076 | positive |
| *Escherichia coli* | O157 | H7 | DSM_19206 | positive |

Example 2

Figure 2:
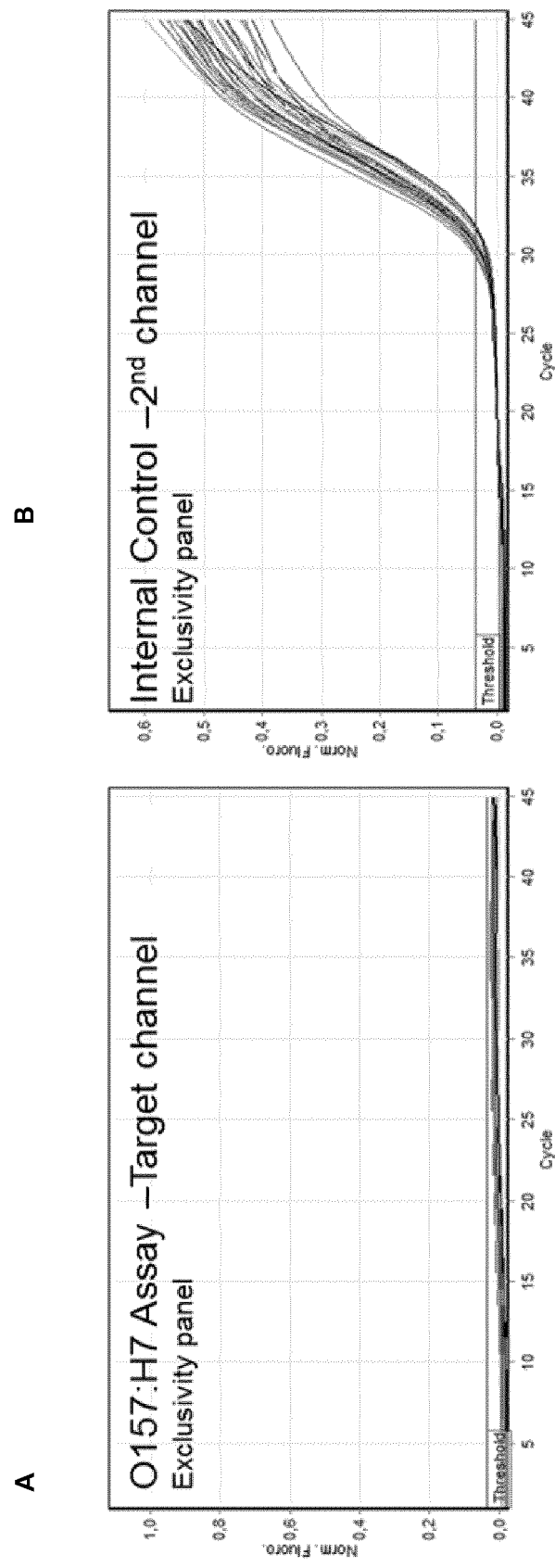
FIG. 2.
Figure 3:
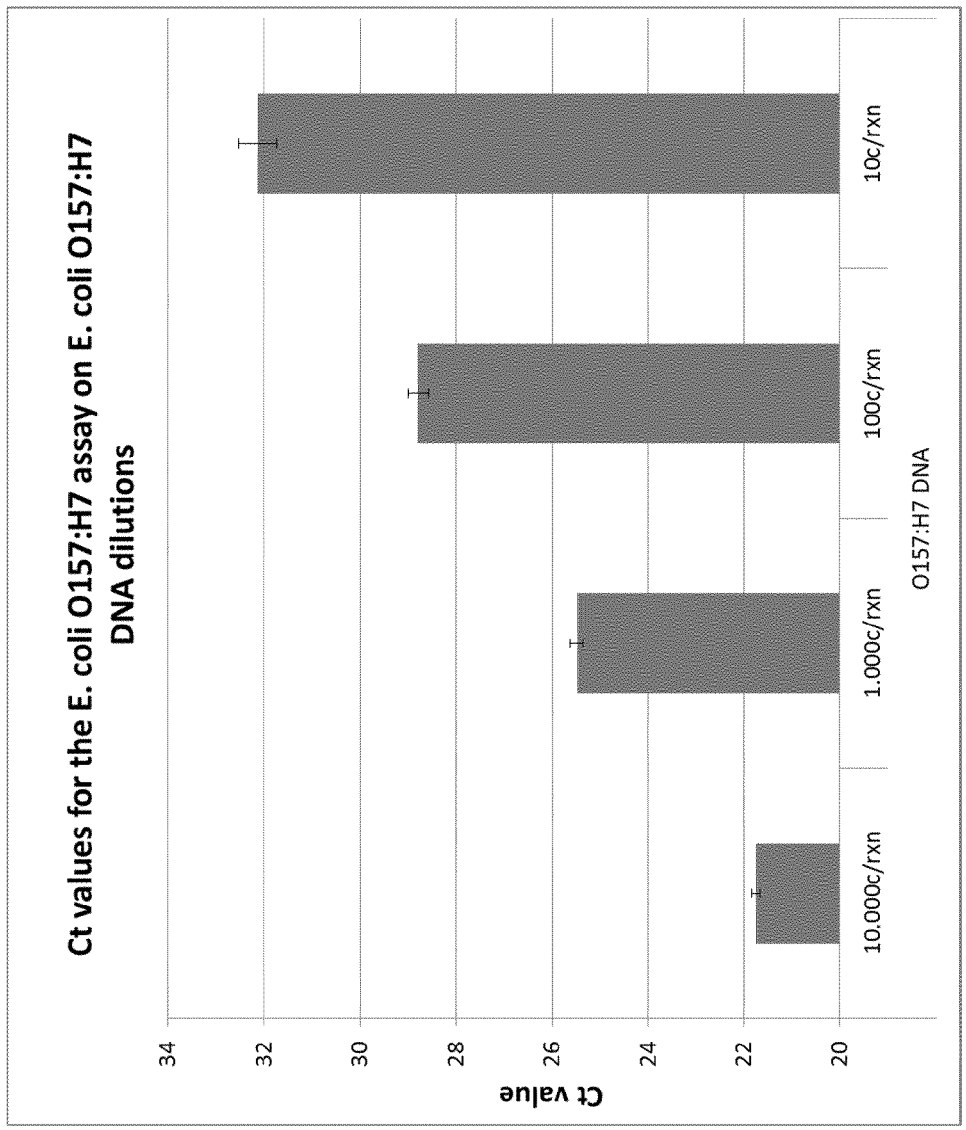
FIG. 3.
Figure 4:
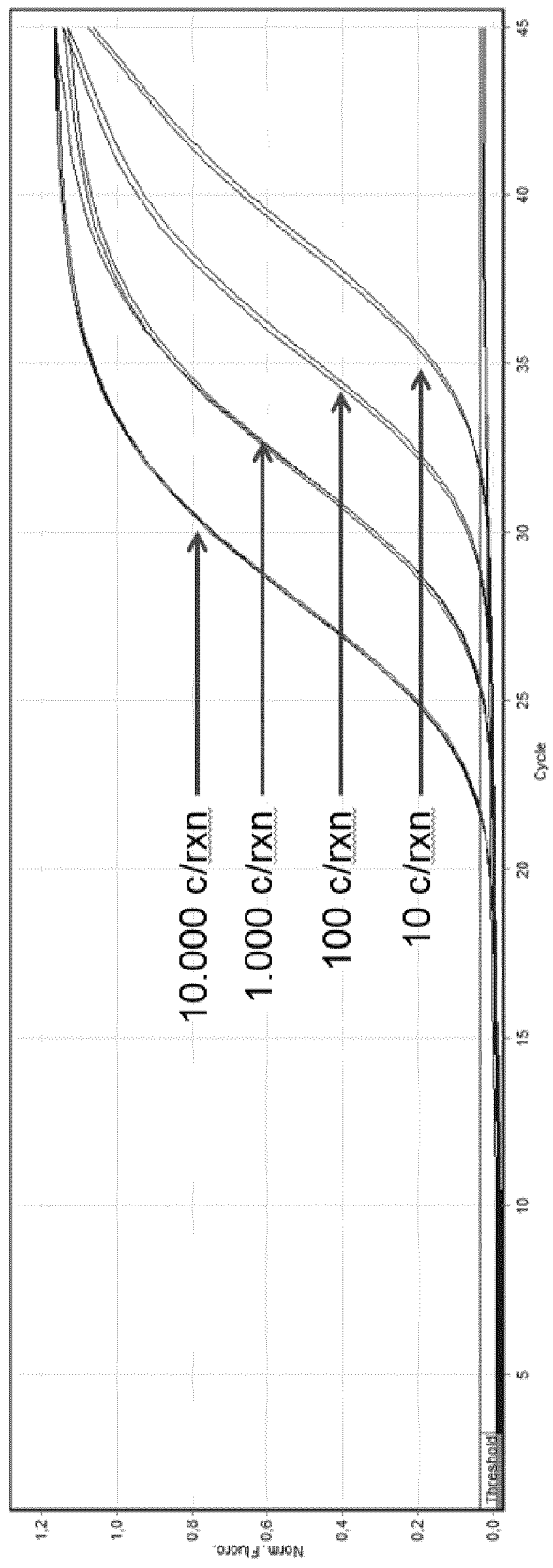
FIG. 4.

Exclusivity tests are carried out in Example 2 and illustrated in FIG. 2. In this context, exclusivity is defined as the correct lack of signal of non-target DNA samples (FIG. 2A), and correct positive signal of the internal amplification control (FIG. 2B), which implicate absence of the target pathogen O157:H7 (FIG. 2A). The internal amplification control comprises an artificial plasmid, corresponding primers, and a probe, which are added to the reaction mix, whereby said internal control demonstrates that the PCR works correctly when positive results are achieved for the *E. coli* exclusivity test (FIG. 2B).

The strains used in the exclusivity tests are shown in Table 2.

TABLE 2

| Organism | O group | H group | source (if known) | comments | test result |
|---|---|---|---|---|---|
| *Escherichia coli* | O1 | H7 | | DSM_30083 | negative |
| *Escherichia coli* | O1:K1 | H7 | | DSM_10750 | negative |
| *Escherichia coli* | O103 | H- | | DSM_10233 | negative |
| *Escherichia coli* | O111 | H- | | DSM_8698 | negative |
| *Escherichia coli* | O121 | H7 | human | | negative |
| *Escherichia coli* | O121 | H7 | beef | | negative |
| *Escherichia coli* | O121 | | | NC09121 | negative |
| *Escherichia coli* | O145 | | | SSI 82280 | negative |
| *Escherichia coli* | O153 | H7 | rabbit | | negative |
| *Escherichia coli* | O157 | H16 | | CDC 3006-89 9/94 | negative |
| *Escherichia coli* | O157 | H45 | | CDC 3260-96 03/09/00 | negative |
| *Escherichia coli* | O157 | H38 | | HEALTH CANADA 03/14/00 | negative |
| *Escherichia coli* | O157 | H38 | | WILD 03/09/00 | negative |
| *Escherichia coli* | O157 | H19 | | CDC 1924-82 03/09/00 | negative |
| *Escherichia coli* | O157 | NM | | *E. coli* ref. Center 0.0372 | negative |
| *Escherichia coli* | O18ac:K1 | H7 | | DSM_10723 | negative |
| *Escherichia coli* | O19 | H7 | | DSM_11752 | negative |
| *Escherichia coli* | O26 | H7 | human | | negative |
| *Escherichia coli* | O26 | H- | | DSM_8695 | negative |
| *Escherichia coli* | O45 | | | SSI 81886 | negative |
| *Escherichia coli* | O55 | H7 | | *E. coli* ref. Center 10.0728 | negative |
| *Escherichia coli* | O55 | H7 | | *E. coli* ref. Center 9.0106 | negative |
| *Escherichia coli* | O55 | H7 | | ECRC EQ5624-50 6/96 | negative |
| *Escherichia coli* | O7:K1 | H7 | | DSM_10858 | negative |
| *Escherichia coli* VTEC T3 (stx1) | | | | RM_DNA_120 | negative |
| *Escherichia coli* VTEC T6 (stx2) | | | | RM_DNA_119 | negative |

Example 1

DNA isolated from *E. coli* O157:NM/H7 or O157:H7, and specified in Table 1, is hybridized with a primer pair, the forward-primer having SEQ ID NO:1, the reverse primer having SEQ ID NO: 5. and a TaqMan probe having SEQ ID NO:8 (illustrated in FIG. 1A). Also, an internal amplification control is carried out (illustrated in FIG. 1B). The internal amplification control comprises an artificial plasmid, corresponding primers, and a probe, which are added to the reaction mix, whereby said internal control demonstrates that the PCR works correctly when positive results are achieved for the *E. coli* inclusivity test and negative results are achieved for the exclusivity test (FIG. 1B). A real-time PCR reaction is conducted over 45 cycles and the fluorescence of both PCR systems is measured online (FIGS. 1A and 1B).

A real-time PCR reaction assay is conducted with DNA selected from non-*E. coli* serotypes of any of the following: O1:H7, O1:K1:H7, O19:H7, O26:H-, 026:H7, O45:H-SSI 81886, O55:H7 *E. coli* ref. Center 10.0728, O55:H7 *E. coli* ref. Center 9.0106, O55:H7 ECRC EQ5624-50 6/96, O7:K1:H7, O103:H-, O111:H-, O121:H7 from human, O121:H7 from beef, O121 NC09121, O145 SSI 82280, 0153:H7 from rabbit, O157:H16, O157:H19, O157:H38 HEALTH CANADA 03/14/00, O157:H38 WILD 03/09/00, O157:H45, O157:H19 CDC 1924-82 03/09/00, O157:NM, 018ac:K1:H7, *Escherichia coli* VTEC T3 (stx1), or *Escherichia coli* VTEC T6 (stx2)(specified in Table 2) and a primer pair for DNA amplification, with the forward primer oligonucleotide having SEQ ID NO:1, the reverse primer having SEQ ID NO:5.

The hybridization probe is a TaqMan probe having the SEQ ID NO:8 and comprising a fluorescent dye and a fluorescence quencher. An internal amplification control used in the exclusivity panel comprises an artificial plasmid, to which the corresponding primers and probe are added The real-time PCR assay is conducted over 45 cycles and the fluorescence of both PCR systems is measured online (FIGS. 2a and 2b).

Example 3

DNA from *E. coli* O157:H7-serotype (DSM 13526) with dilutions having 10, 100, 1,000, and 10,000 copies of DNA per reaction were subjected to real-time PCR reaction, wherein the forward primer is SEQ ID NO:1, the reverse primer is SEQ ID NO:5 for DNA amplification. The hybridization probe is a TaqMan probe having SEQ ID NO:8. The real-time PCR assay is conducted over 45 cycles and the fluorescence is measured online.

Example 4

Reactions for the inclusivity testing of O145:H28 over non-O145:H28 serotypes or O157:H7 and O145:H28 over other *E. coli* serotypes were prepared with QuantiFast Multiplex PCR Mastermix (QIAGEN), 0.4 µM forward and 0.4 µM reverse Primer, 0.2 µM TaqMan Probe DNA and water in a 20 µl reaction volume.

The number of cycles for the amplification reaction was 40 cycles. Cycling profile was 5 min 95° C. followed by a 3-step cycle of 15 sec 95° C., 15 sec 60° C., 10 sec 72° C. in a Rotor-Gene Q.

TaqMan probe used in the reactions has SEQ ID NO:8 (1$^{st}$ and 3$^{rd}$ columns from the right in Table 3) or SEQ ID NO:9 (2$^{nd}$ column from the right in Table 3), linked to Cy5.5 and 3BHQ2 at 5' and 3' termini, respectively. The primer pairs were selected as follows. For O145:H28 detection over non-O145:H28 *E. coli* serotypes a forward primer of SEQ ID NO:12 was combined with a reverse primer of SEQ ID NO:5. Alternatively, for O145:H28 detection over non-O145:H28 serotypes a forward primer of SEQ ID NO: 3 was combined with a reverse primer of SEQ ID NO:13. For the selective detection of O145:H28 and O157:H7 forward primer of SEQ ID NO: 3 was combined with reverse primer of SEQ ID NO:5.

The strains used in the inclusivity tests are shown in Table 3.

TABLE 3

| Organism | O group | H group | source (if known) | comments | combination Seq ID No. 12/5/8 | combination Seq ID No. 3/13/9 | combination Seq ID No. 3/5/8 |
|---|---|---|---|---|---|---|---|
| *Escherichia coli* | O1 | H7 | | DSM_30083 | negative | negative | negative |
| *Escherichia coli* | O1:K1 | H7 | | DSM_10750 | negative | negative | negative |
| *Escherichia coli* | O103 | H- | | DSM_10233 | negative | negative | negative |
| *Escherichia coli* | O111 | H- | | DSM_8698 | negative | negative | negative |
| *Escherichia coli* | O121 | H7 | human | | negative | negative | negative |
| *Escherichia coli* | O121 | H7 | beef | | negative | negative | negative |
| *Escherichia coli* | O121 | | | NC09121 | negative | negative | negative |
| *Escherichia coli* | O153 | H7 | rabbit | | negative | negative | negative |
| *Escherichia coli* | O157 | H16 | | CDC 3006-89 9/94 | negative | negative | negative |
| *Escherichia coli* | O157 | H45 | | CDC 3260-96 03/09/00 | negative | negative | negative |
| *Escherichia coli* | O157 | H38 | | HEALTH CANADA 03/14/00 | negative | negative | negative |
| *Escherichia coli* | O157 | H38 | | WILD 03/09/00 | negative | negative | negative |
| *Escherichia coli* | O157 | H19 | | CDC 1924-82 03/09/00 | negative | negative | negative |
| *Escherichia coli* | O157 | NM | | *E. coli* ref. Center 0.0372 | negative | negative | negative |
| *Escherichia coli* | O18ac:K1 | H7 | | DSM_10723 | negative | negative | negative |
| *Escherichia coli* | O19 | H7 | | DSM_11752 | negative | negative | negative |
| *Escherichia coli* | O26 | H7 | human | | negative | negative | negative |
| *Escherichia coli* | O26 | H- | | DSM_8695 | negative | negative | negative |
| *Escherichia coli* | O45 | | | SSI 81886 | negative | negative | negative |
| *Escherichia coli* | O55 | H7 | | *E. coli* ref. Center 10.0728 | negative | negative | negative |
| *Escherichia coli* | O55 | H7 | | *E. coli* ref. Center 9.0106 | negative | negative | negative |
| *Escherichia coli* | O55 | H7 | | ECRC EQ5624-50 6/96 | negative | negative | negative |
| *Escherichia coli* | O7:K1 | H7 | | DSM_10858 | negative | negative | negative |
| *Escherichia coli* VTEC T3 (stx1) | | | | RM_DNA_120 | negative | negative | negative |
| *Escherichia coli* VTEC T6 (stx2) | | | | RM_DNA_119 | negative | negative | negative |
| *Escherichia coli* | O145 | | | SSI 82280 | positive | positive | positive |
| *Escherichia coli* | O157 | NM | | *E. coli* ref. Center 0.0373 | negative | negative | positive |
| *Escherichia coli* | O157 | NM | | *E. coli* ref. Center 88.1041 | negative | negative | positive |
| *Escherichia coli* | O157 | H7 | | DSM_8579 | negative | negative | positive |
| *Escherichia coli* | O157 | H7 | | DSM_13526 | negative | negative | positive |
| *Escherichia coli* | O157 | H7 | | DSM_17076 | negative | negative | positive |
| *Escherichia coli* | O157 | H7 | | DSM_19206 | negative | negative | positive |

Example 5

Reactions for testing the sensitivity of the O157:H7 detection method were set up according to the following scheme:

10 µl 2× reconstituted PCR-Assay containing specific Primers/Probe, dNTPs, HotStarTaq Plus DNA Polymerase and dedicated multiplex Realtime-PCR buffer+10 µl sample DNA (or positive, or negative control)

Cycling profile:
5 min 95° C. Initial PCR activation step followed by
3-step cycling (40-45 cycles)
15 s 95° C. Denaturation
15 s 60° C. Annealing
10 s 72° C. Extension Real-time PCR reactions were conducted with dilutions of O157:H7 DNA, which contain 10, 100, 1,000, or 10,000 copies of O157:H7 DNA template. The corresponding Ct-values were determined.

TABLE 4

| Sequence no | Sequence (5'-3') |
|---|---|
| 1 | gtttaactcggaagtgatgt |
| 2 | actcggaagtgatgtgattg |
| 3 | tgatacgtttgtgattcataataactc |
| 4 | ctgtttctttagagtaaatgtatg |
| 5 | catccgacctgtttctttagag |
| 6 | Gtccagcaatcacatcactt |
| 7 | /5Cy5.5/tggacagcctgaagagagaggggat/3BHQ2/ |
| 8 | /5Cy5.5/ctggacagcctgaagagagagg/3BHQ2/ |
| 9 | /5Cy5.5/gaagaatgccggtcgtttaactcgg/3BHQ2/ |
| 10 | ccttctattg atcttggtga ttttcttca tcaatagcag cttgcaagat cataactatt tctgaattta atgagcgtcc gttttcgat gctcttatgg tcaggtcgcg cttgaggcta tctggcattc ttacgctata tggggctatg tctctaacct tcgtcatact tacaccgtga taatcacatt gatatcacag tgtattcaaa aaaactttga cttgatatag tcacagtgat acgtttgtga ttcataataa ctcacgcggt ggcgatatgg aaaagaagt tagcagaatt ttggtgagaa tacctcagtc gctaaaagat gcgattacag gaaaggccaa agaagaatgc cggtcgttta actcggaagt gatgtgattg ctggacagcc tgaagagaga ggggataacg gtatgagtaa agaatgttgt tttttgcggc attagcgaat cagacgctga tcaaacatac atttactcta aagaaacagg tcggatgctg tgtagtgact gcgtgtttga catcataaga tacaagtatc ttggatgttc tgccagcatt |
| 11 | agcaatatag gtgaagtgta cgaagggaaag atataactga tagagcagaa agttgaagcc ccaactgctg taacagtcag ggcttcgtta tcaacaaatc ggcttaggaa atattgacat gaaaagtat |
| 11 | ccttctattga tcttggtgat ttttcttcat caatagcagc ttgcaagatc ataactattt ctgaattaa tgagcgtccg ttttcgatg ctcttatggt caggtcgcgc ttgaggctat ctggcattct tacgctatat ggggctatgt ctctaacctt cgtcatactt acaccgtgat aatcacattg atatcacagt gtattcaaaa aaactttgac ttgatatagt cacagtgata cgtttgtgat tcataataac tcacgcggtg gcgatatgga aaagaagtt agcagaattt tggtgagaat gcctcagtcg ctaaaagatg cgattacagg aaaggccaaa gaagaatgcc ggtcgtttaa ctcggaagtg attaagcgat tgctggacag cctgaagaga gagggataa cggtatgagt aaagaatgtt gttttttgcg gcattagcga atcagacgct gatcaaacat acatttactc taaagaaaca ggtcggatgc tgtgtagtga ctgcgtgttt gacatcataa gatacaagta tcttggatgt tctgccagca ttagcaatat aggtgaagtg tacgaaggga aagatataac tgatagagca gaaagttgaa gccccaactg ctgtaacagt cagggcttcg ttatcaacaa atcggcttag gaaatattga catgaaaagt at |
| 12 | taactcggaagtgattaagcgatt |
| 13 | gtccagcaatcgcttaat |
| 14 | cggtcgttta actcggaagt gatgt |

The invention claimed is:

1. A method of detecting *E. coli* serotype O157:H7 in a sample, the method comprising:
   (a) obtaining a sample;
   (b) detecting whether *E. coli* serotype O157:H7 is present in the sample by performing an amplification reaction using at least one oligonucleotide as an amplification primer, wherein the oligonucleotide has a nucleotide sequence that is at least 90% identical to a nucleotide sequence of the same length within SEQ ID NO: 10 or to the complement of the nucleotide sequence of the same length, and wherein the oligonucleotide further comprises: (i) nucleotides 382-385 of SEQ ID NO: 10 or the complement thereof, (ii) nucleotides 382-384 of SEQ ID NO: 10 or the complement thereof, or (iii) nucleotides 383-385 of SEQ ID NO: 10 or the complement thereof, and wherein the oligonucleotide has a length of about 10-100, about 10-50 nucleotides, about 10-30 nucleotides, or 18-27 nucleotides; and
   (c) determining the presence of a *E. coli* serotype O157:H7 in the sample.

2. The method of claim 1, wherein the oligonucleotide has a nucleotide sequence that is at least 95%, 98%, 99% identical or is identical to a nucleotide sequence of the same length within SEQ ID NO: 10, or to the complement of said nucleotide sequence of the same length.

3. The method of claim 1, wherein the oligonucleotide is covalently or noncovalently attached to a label.

4. The method of claim 3, wherein the label is a fluorescent dye.

5. The method of claim 1, wherein the oligonucleotide comprises SEQ ID NOs: 1, 2 or 6.

6. The method of claim 1, wherein the amplification reaction is a polymerase chain reaction.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
gtttaactcg gaagtgatgt     20

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
actcggaagt gatgtgattg     20

<210> SEQ ID NO 3
<211> LENGTH: 27
<212> TYPE: DNA
<213> ORGANISM: artificial sequence
<220> FEATURE:
<223> OTHER INFORMATION: primer

<400> SEQUENCE: 3
tgatacgttt gtgattcata ataactc                                27

<210> SEQ ID NO 4
<211> LENGTH: 24
<212> TYPE: DNA
<213> ORGANISM: artificial sequence
<220> FEATURE:
<223> OTHER INFORMATION: primer

<400> SEQUENCE: 4
ctgtttcttt agagtaaatg tatg                                   24

<210> SEQ ID NO 5
<211> LENGTH: 22
<212> TYPE: DNA
<213> ORGANISM: artificial sequence
<220> FEATURE:
<223> OTHER INFORMATION: primer

<400> SEQUENCE: 5
catccgacct gtttctttag ag                                     22

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
gtccagcaat cacatcactt                                        20

<210> SEQ ID NO 7
<211> LENGTH: 25
<212> TYPE: DNA
<213> ORGANISM: artificial sequence
<220> FEATURE:
<223> OTHER INFORMATION: TaqMan probe
<220> FEATURE:
<221> NAME/KEY: modified_base
<222> LOCATION: 1
<223> OTHER INFORMATION: /mod_base="OTHER"
    /note="Cy5.5"
<220> FEATURE:
<221> NAME/KEY: modified_base
<222> LOCATION: 25
<223> OTHER INFORMATION: /mod_base="OTHER"
    /note="BHQ2"

<400> SEQUENCE: 7
tggacagcct gaagagagag gggat                                  25

<210> SEQ ID NO 8
<211> LENGTH: 23
<212> TYPE: DNA
<213> ORGANISM: artificial sequence
<220> FEATURE:
<223> OTHER INFORMATION: TaqMan probe
<220> FEATURE:
<221> NAME/KEY: modified_base
<222> LOCATION: 1
<223> OTHER INFORMATION: /mod_base="OTHER"
    /note="Cy5.5"
<220> FEATURE:
<221> NAME/KEY: modified_base
<222> LOCATION: 23
<223> OTHER INFORMATION: /mod_base="OTHER"
    /note="BHQ2"

```
<400> SEQUENCE: 8
ctggacagcc tgaagagaga ggg                                             23

<210> SEQ ID NO 9
<211> LENGTH: 25
<212> TYPE: DNA
<213> ORGANISM: artificial sequence
<220> FEATURE:
<223> OTHER INFORMATION: TaqMan probe
<220> FEATURE:
<221> NAME/KEY: modified_base
<222> LOCATION: 1
<223> OTHER INFORMATION: /mod_base="OTHER"
      /note="Cy5.5"
<220> FEATURE:
<221> NAME/KEY: modified_base
<222> LOCATION: 25
<223> OTHER INFORMATION: /mod_base="OTHER"
      /note="BHQ2"

<400> SEQUENCE: 9
gaagaatgcc ggtcgtttaa ctcgg                                           25

<210> SEQ ID NO 10
<211> LENGTH: 700
<212> TYPE: DNA
<213> ORGANISM: Escherichia coli O157:H7 str. EDL933
<220> FEATURE:
<223> OTHER INFORMATION: 1576501-1576700

<400> SEQUENCE: 10
ccttctattg atcttggtga tttttcttca tcaatagcag cttgcaagat cataactatt      60
tctgaattta atgagcgtcc gttttcgat gctcttatgg tcaggtcgcg cttgaggcta     120
tctggcattc ttacgctata tggggctatg tctctaacct tcgtcatact tacaccgtga    180
taatcacatt gatatcacag tgtattcaaa aaaactttga cttgatatag tcacagtgat    240
acgtttgtga ttcataataa ctcacgcggt ggcgatatgg aaaagaagt tagcagaatt     300 ttggtgagaa tacctcagtc gctaaaagat gcgattacag gaaaggccaa agaagaatgc    360
cggtcgttta actcggaagt gatgtgattg ctggacagcc tgaagagaga ggggataacg    420
gtatgagtaa agaatgttgt tttttgcggc attagcgaat cagacgctga tcaaacatac    480
atttactcta aagaaacagg tcggatgctg tgtagtgact gcgtgtttga catcataaga    540
tacaagtatc ttggatgttc tgccagcatt agcaatatag gtgaagtgta cgaagggaaa    600
gatataactg atagagcaga aagttgaagc cccaactgct gtaacagtca gggcttcgtt    660
atcaacaaat cggcttagga aatattgaca tgaaaagtat                          700

<210> SEQ ID NO 11
<211> LENGTH: 703
<212> TYPE: DNA
<213> ORGANISM: Escherichia coli O145:H28
<220> FEATURE:
<223> OTHER INFORMATION: 1601882-1602584

<400> SEQUENCE: 11
ccttctattg atcttggtga tttttcttca tcaatagcag cttgcaagat cataactatt      60
tctgaattta atgagcgtcc gttttcgat gctcttatgg tcaggtcgcg cttgaggcta     120
tctggcattc ttacgctata tggggctatg tctctaacct tcgtcatact tacaccgtga    180
taatcacatt gatatcacag tgtattcaaa aaaactttga cttgatatag tcacagtgat    240
```

```
acgtttgtga ttcataataa ctcacgcggt ggcgatatgg aaaaagaagt tagcagaatt    300
ttggtgagaa tgcctcagtc gctaaaagat gcgattacag gaaaggccaa agaagaatgc    360
cggtcgttta actcggaagt gattaagcga ttgctggaca gcctgaagag agaggggata    420
acggtatgag taaagaatgt tgttttttgc ggcattagcg aatcagacgc tgatcaaaca    480
tacatttact ctaaagaaac aggtcggatg ctgtgtagtg actgcgtgtt tgacatcata    540
agatacaagt atcttggatg ttctgccagc attagcaata taggtgaagt gtacgaaggg    600
aaagatataa ctgatagagc agaaagttga agccccaact gctgtaacag tcagggcttc    660
gttatcaaca aatcggctta ggaaatattg acatgaaaag tat                      703

<210> SEQ ID NO 12
<211> LENGTH: 24
<212> TYPE: DNA
<213> ORGANISM: artificial sequence
<220> FEATURE:
<223> OTHER INFORMATION: primer

<400> SEQUENCE: 12
taactcggaa gtgattaagc gatt                                            24

<210> SEQ ID NO 13
<211> LENGTH: 18
<212> TYPE: DNA
<213> ORGANISM: artificial sequence
<220> FEATURE:
<223> OTHER INFORMATION: primer

<400> SEQUENCE: 13
gtccagcaat cgcttaat                                                   18

<210> SEQ ID NO 14
<211> LENGTH: 25
<212> TYPE: DNA
<213> ORGANISM: artificial sequence
<220> FEATURE:
<223> OTHER INFORMATION: primer

<400> SEQUENCE: 14
cggtcgttta actcggaagt gatgt                                           25
```